United States Patent [19]

Hayashi et al.

[11] Patent Number: 5,767,940
[45] Date of Patent: Jun. 16, 1998

[54] OPHTHALMIC APPARATUS

[75] Inventors: Akihiro Hayashi, Toyokawa; Yoshinobu Hosoi, Gamagori, both of Japan

[73] Assignee: Nidek Co., Ltd., Japan

[21] Appl. No.: 739,780

[22] Filed: Oct. 30, 1996

[30] Foreign Application Priority Data

Oct. 31, 1995 [JP] Japan .................................. 7-308439
Jul. 25, 1996 [JP] Japan .................................. 8-215056

[51] Int. Cl.[6] .................................................. A61B 3/10
[52] U.S. Cl. ........................................ 351/205; 351/24
[58] Field of Search ................................ 351/205, 206, 351/211, 222

[56] References Cited

U.S. PATENT DOCUMENTS 5,270,749 12/1993 Okumura ................................. 351/205
5,309,186  5/1994 Mizuno .................................. 351/212
5,444,504  8/1995 Kobayashi et al. ..................... 351/237

FOREIGN PATENT DOCUMENTS 6-254050 9/1994 Japan.
6-339462 12/1994 Japan.

*Primary Examiner*—Huy Mai
*Attorney, Agent, or Firm*—Finnegan, Henderson, Farabow, Garrett & Dunner, L.L.P.

[57] ABSTRACT

An ophthalmic apparatus for obtaining a refractive corrected power based on a refractive power that an eye to be examined has, the apparatus comprises input device for inputting data of objective values obtained by measuring objectively the refractive power of the eye to be examined and information of adjustment factors for adjusting a corrected power, program storing device for storing a program in order to adjust the corrected power against the data of objective values based on the data inputted by the input device and for expecting a prescribed power, executing device for executing the program stored in the program storing device, prescribed power calculating device for calculating an expected-prescribed power in response to the program executed by the executing device, and displaying device for displaying the expected-prescribed power calculated by the prescribed power calculating device.

28 Claims, 29 Drawing Sheets

FIG. 3

|  |  | S | C | A |
|---|---|---|---|---|
| M | R | -1.75 | -0.75 | 0 |
|  | L | -2.25 | -0.25 | 0 |
| AR | R | -3.00 | -1.50 | 175 |
|  | L | -3.50 | -1.00 | 5 |
| FINAL | R | — | — | — |
|  | L | — | — | — |

FIG. 4 (b)

| 1-1 · · · · · Astigmatism ? |
|---|
| 1-2 · · · · · Oblique astigmatism ? |
| 1-3 · · · · · S value ? |
| 1-4 · · · · · S value ? |
| 1-5 · · · · · S value ? |

FIG. 5 (b)

| | |
|---|---|
| A-1 ····· | Initial spectacles wear ? |
| A-2 ····· | Difference in S between right and left $\leqq$ 0.75 ? |
| A-3 ····· | Strong S = Weak S + 0.75 |
| A-4 ····· | Difference in S between right and left $\leqq$ 0.75 ? |
| A-5 ····· | Strong S = the larger one between the absolute value of "Weak S + 0.75" and that of "Previous S + 0.75" (not more than the objective) |
| B-1 ····· | Initial spectacles wear ? |
| B-2 ····· | Weak S eye standard<br>Table A<br>Effect $\Delta$ S1 subtraction process on both eyes |
| B-3 ····· | Difference in S between right and left $\leqq$ 0.75 ? |
| B-4 ····· | Strong S = Weak S − 0.75 |
| B-5 ····· | Weak S eye standard<br>Table B<br>Effect $\Delta$ S2 subtraction process on both eyes |
| B-6 ····· | Difference in S between right and left $\leqq$ 0.75 ? |
| B-7 ····· | Strong S = the larger one between the absolute value of "Weak S − 0.75" and that of "Previous S − 0.75" (not more than the objective) |

F I G. 6 (b)

| | |
|---|---|
| C-1 ····· | Initial spectacles wear ? |
| C-2 ····· | Weak C eye standard<br>Table C<br>Effect $\Delta$ C1 subtraction process on both eyes |
| C-3 ····· | Add $\Delta$ C1/2 to S (binocular equivalent spherical surface) |
| C-4 ····· | Difference in S between right and left $\leq$ 0.75 ? |
| C-5 ····· | Strong S = Weak S + 0.75 |
| C-6 ····· | Difference in C between right and left $\leq$ 0.75 ? |
| C-7 ····· | Strong C = Weak C − 0.75 |

FIG. 6 (c)

| | |
|---|---|
| C-8 ····· | Previous spectacles C ? |
| C-9 ····· | Weak C eye standard<br>Table D<br>Effect  Δ C2 subtraction process on both eyes |
| C-10 ···· | Add  Δ C2/2 to S (binocular equivalent spherical surface) |
| C-11 ···· | Difference in S between right and left  ≦  0.75 ? |
| C-12 ···· | Strong S = the larger one between the absolute value of<br>"Weak S + 0.75" and that of "Previous S + 0.75"<br>(not more than the objective) |
| C-13 ···· | Difference in C between right and left  ≦  0.75 ? |
| C-14 ···· | Strong C = the larger one between the absolute value of<br>"Weak C − 0.75" and that of "Previous C − 0.75"<br>(not more than the objective) |
| C-15 ···· | Weak C eye standard<br>Table C<br>Effect  Δ C1 subtraction process on both eyes |
| C-16 ···· | Add  Δ C1/2 to S (binocular equivalent spherical surface) |
| C-17 ···· | Difference in S between right and left  ≦  0.75 ? |
| C-18 ···· | Strong S = the larger one between the absolute value of<br>"Weak S + 0.75" and that of "Previous S + 0.75"<br>(not more than the objective) |
| C-19 ···· | Difference in C between right and left  ≦  0.75 ? |
| C-20 ···· | Strong C = Weak C − 0.75 |

F I G. 7 (b)

| | |
|---|---|
| D-1 ····· | Initial spectacles wear ? |
| D-2 ····· | Weak C eye standard<br>Table C<br>Effect $\Delta$ C1 subtraction process on both eyes |
| D-3 ····· | Weak S eye standard<br>Table A<br>Effect $\Delta$ S1 subtraction process on both eyes |
| D-4 ····· | Difference in S between right and left $\leq$ 0.75 ? |
| D-5 ····· | Strong S = Weak S - 0.75 |
| D-6 ····· | Difference in C between right and left $\leq$ 0.75 ? |
| D-7 ····· | Strong C = Weak C - 0.75 |

FIG. 7 (c)

| | |
|---|---|
| D-8 ····· | Previous spectacles C ? |
| D-9 ····· | Weak C eye standard<br>Table D<br>Effect  Δ C2 subtraction process on both eyes |
| D-10 ···· | Weak S eye standard<br>Table B<br>Effect  Δ S2 subtraction process on both eyes |
| D-11 ···· | Difference in S between right and left ≦ 0.75 ? |
| D-12 ···· | Strong S = the larger one between the absolute value of<br>"Weak S − 0.75" and that of "Previous S − 0.75"<br>(not more than the objective) |
| D-13 ···· | Difference in C between right and left ≦ 0.75 ? |
| D-14 ···· | Strong C = the larger one between the absolute value of<br>"Weak C − 0.75" and that of "Previous C − 0.75"<br>(not more than the objective) |
| D-15 ···· | Weak C eye standard<br>Table C<br>Effect  Δ C1 subtraction process on both eyes |
| D-16 ···· | Weak S eye standard<br>Table B<br>Effect  Δ S2 subtraction process on both eyes |
| D-17 ···· | Difference in S between right and left ≦ 0.75 ? |
| D-18 ···· | Strong S = the larger one between the absolute value of<br>"Weak S − 0.75" and that of "Previous S − 0.75"<br>(not more than the objective) |
| D-19 ···· | Difference in C between right and left ≦ 0.75 ? |
| D-20 ···· | Strong C = Weak C − 0.75 |

F I G. 8 (b)

| E-1 | Initial spectacles wear ? |
|---|---|
| E-2 | C = -0.25 or -0.50 ? |
| E-3 | C = 0<br>Add C/2 to S (equivalent spherical surface) |
| E-4 | Difference in S between right and left $\leq$ 0.75 ? |
| E-5 | Strong S = Weak S + 0.75 |
| E-6 | Weak C eye standard<br>Table C<br>Effect $\Delta$ C1 subtraction process on both eyes |
| E-7 | Add $\Delta$ C1/2 to S (binocular equivalent spherical surface) |
| E-8 | Difference in S between right and left $\leq$ 0.75 ? |
| E-9 | Strong S = Weak S + 0.75 |
| E-10 | Difference in C between right and left $\leq$ 0.75 ? |
| E-11 | Strong C = Weak C - 0.75 |

FIG. 8 (c)

| | |
|---|---|
| E-12 · · · · | C = −0.25 or −0.50 ? |
| E-13 · · · · | Previous spectacles C ? |
| E-14 · · · · | Previous spectacles C ? |
| E-15 · · · · | C = 0<br>Add C/2 to S (equivalent spherical surface) |
| E-16 · · · · | Difference in S between right and left ≦ 0.75 ? |
| E-17 · · · · | Strong S = the larger one between the absolute value of<br>"Weak S + 0.75" and that of "Previous S + 0.75"<br>(not more than the objective) |
| E-18 · · · · | Weak C eye standard<br>Table D<br>Effect Δ C2 subtraction process on both eyes |
| E-19 · · · · | Add Δ C2/2 to S (binocular equivalent spherical surface) |
| E-20 · · · · | Difference in S between right and left ≦ 0.75 ? |
| E-21 · · · · | Strong S = the larger one between the absolute value of<br>"Weak S + 0.75" and that of "Previous S + 0.75"<br>(not more than the objective) |
| E-22 · · · · | Difference in C between right and left ≦ 0.75 ? |
| E-23 · · · · | Strong C = the larger one between the absolute value of<br>"Weak C − 0.75" and that of "Previous C − 0.75"<br>(not more than the objective) |

FIG. 8 (d)

| | |
|---|---|
| E-24 · · · · | Weak C eye standard<br>Table C<br>Effect Δ C1 subtraction process on both eyes |
| E-25 · · · · | Add Δ C1/2 to S (binocular equivalent spherical surface) |
| E-26 · · · · | Difference in S between right and left ≦ 0.75 ? |
| E-27 · · · · | Strong S = the larger one between the absolute value of<br>"Weak S + 0.75" and that of "Previous S + 0.75"<br>(not more than the objective) |
| E-28 · · · · | Difference in C between right and left ≦ 0.75 ? |
| E-29 · · · · | Strong C = Weak C − 0.75 |

FIG. 9 (b)

| | |
|---|---|
| F-1 ····· | Initial spectacles wear ? |
| F-2 ····· | C = −0.25 or −0.50 ? |
| F-3 ····· | C = 0 |
| F-4 ····· | Weak C eye standard<br>Table A<br>Effect Δ S1 subtraction process on both eyes |
| F-5 ····· | Difference in S between right and left ≦ 0.75 ? |
| F-6 ····· | Strong S = Weak S − 0.75 |
| F-7 ····· | Weak C eye standard<br>Table C<br>Effect Δ C1 subtraction process on both eyes |
| F-8 ····· | Weak S eye standard<br>Table A<br>Effect Δ S1 subtraction process on both eyes |
| F-9 ····· | Difference in S between right and left ≦ 0.75 ? |
| F-10 ···· | Strong S = Weak S − 0.75 |
| F-11 ···· | Difference in C between right and left ≦ 0.75 ? |
| F-12 ···· | Strong C = Weak C − 0.75 |

FIG. 9 (c)

| | |
|---|---|
| F-13 · · · · | C = -0.25 or -0.50 ? |
| F-14 · · · · | Previous spectacles C ? |
| F-15 · · · · | Previous spectacles C ? |
| F-16 · · · · | C = 0 |
| F-17 · · · · | Weak S eye standard<br>Table B<br>Effect  Δ S2 subtraction process on both eyes |
| F-18 · · · · | Difference in S between right and left  ≦  0.75 ? |
| F-19 · · · · | Strong S = the larger one between the absolute value of<br>"Weak S − 0.75" and that of "Previous S − 0.75"<br>(not more than the objective) |
| F-20 · · · · | Weak C eye standard<br>Table D<br>Effect  Δ C2 subtraction process on both eyes |
| F-21 · · · · | Weak S eye standard<br>Table B<br>Effect  Δ S2 subtraction process on both eyes |
| F-22 · · · · | Difference in S between right and left  ≦  0.75 ? |
| F-23 · · · · | Strong S = the larger one between the absolute value of<br>"Weak S − 0.75" and that of "Previous S − 0.75"<br>(not more than the objective) |
| F-24 · · · · | Difference in C between right and left  ≦  0.75 ? |
| F-25 · · · · | Strong C = the larger one between the absolute value of<br>"Weak C − 0.75" and that of "Previous C − 0.75"<br>(not more than the objective) |

FIG. 9 (d)

| | |
|---|---|
| F-26 · · · · | Weak C eye standard<br>Table C<br>Effect Δ C1 subtraction process on both eyes |
| F-27 · · · · | Weak S eye standard<br>Table B<br>Effect Δ S2 subtraction process on both eyes |
| F-28 · · · · | Difference in S between right and left ≦ 0.75 ? |
| F-29 · · · · | Strong S = the larger one between the absolute value of "Weak S − 0.75" and that of "Previous S − 0.75" (not more than the objective) |
| F-30 · · · · | Difference in C between right and left ≦ 0.75 ? |
| F-31 · · · · | Strong C = Weak C − 0.75 |

TABLE A <ADJUST DEGREE OF MYOPIA>
[UPON INITIAL SPECTACLES WEAR]

| OBJECTIVE S1 | RECTIFYING-QUANTITY ΔS1 |
|---|---|
| -0.25 | S1/2 (THE CONDITION OF WHICH TO RAISE 0.25D STEP EVERY STEP) |
| -0.50 | |
| -0.75 | |
| -1.00 | |
| -1.25 | |
| -1.50 | |
| -1.75 | |
| -2.00 | |
| -2.25 | |
| -2.50 | |
| -2.75 | |
| -3.00 | |
| -3.25 | |
| -3.50 | |
| -3.75 | |
| -4.00 | |
| -4.25 | |
| -4.50 | |
| -4.75 | |
| -5.00 | |
| ... | |

FIG.10(a)

TABLE B <ADJUST DEGREE OF MYOPIA>
[UPON SECOND TIME SPECTACLES WEAR ~]

| DIFFERENCE BETWEEN PREVIOUS SPECTACLES AND OBJECTIVES — S2 | RECTIFYING-QUANTITY ΔS2 |
|---|---|
| +0.50 | 0 |
| +0.25 | |
| 0 | S2/2 (THE CONDITION OF WHICH TO RAISE 0.25D STEP EVERY STEP) S2+0.75 |
| -0.25 | |
| -0.50 | |
| -0.75 | |
| -1.00 | |
| -1.25 | |
| -1.50 | |
| -1.75 | |
| -2.00 | |
| -2.25 | |
| -2.50 | |
| -2.75 | |
| -3.00 | |
| ... | |

FIG.10(b)

TABLE D <ADJUST DEGREE OF ASTIGMATISM>
[UPON SECOND TIME SPECTACLES WEAR ~]

| C2 | RECTIFYING-QUANTITY ΔC2 |
|---|---|
| +0.50 | |
| +0.25 | 0 |
| 0 | |
| -0.25 | |
| -0.50 | |
| -0.75 | |
| -1.00 | C2/2 |
| -1.25 | (THE CONDITION OF WHICH |
| -1.50 | TO RAISE 0.25D STEP |
| -1.75 | EVERY STEP) |
| -2.00 | |
| -2.25 | C2+0.75 |
| -2.50 | |
| -2.75 | |
| -3.00 | |
| -3.25 | |

DIFFERENCE BETWEEN PREVIOUS SPECTACLES AND OBJECTIVE

FIG.10(d)

TABLE C <ADJUST DEGREE OF ASTIGMATISM>
[UPON INITIAL SPECTACLES WEAR]

| OBJECTIVE C1 | RECTIFYING-QUANTITY ΔC1 |
|---|---|
| -0.25 | |
| -0.50 | |
| -0.75 | |
| -1.00 | |
| -1.25 | |
| -1.50 | C1/2 |
| -1.75 | (THE CONDITION OF WHICH |
| -2.00 | TO RAISE 0.25D STEP |
| -2.25 | EVERY STEP) |
| -2.50 | |
| -2.75 | |
| -3.00 | |
| -3.25 | |
| -3.50 | |
| -3.75 | |

Age  [ 3 8 ]  years old

FIG. 14 (a)

table E

| Myopia power | Unaided eye vision | Myopia power | Unaided eye vision |
|---|---|---|---|
| 0 | 1.0 | -4.25 ~ -5.00 | 0.06 |
| -0.25 | 0.9 | | |
| -0.50 | 0.8 | | |
| -0.75 | 0.7 | -5.25 ~ -7.00 | 0.04 |
| -1.00 | 0.6 | | |
| -1.25 | 0.5 | | |
| -1.50 | 0.4 | -7.25 ~ -9.00 | 0.02 |
| -1.75 | 0.3 | | |
| -2.00 | 0.2 | | |
| -2.25 ~ -3.00 | 0.1 | -9.25 | 0.01 |
| -3.25 ~ -4.00 | 0.08 | | |

FIG. 14 (b)

table F

| Age | Accommodation power (D) | Age | Accommodation power (D) | Age | Accommodation power (D) |
|---|---|---|---|---|---|
| ~10 | 14.00 | | | | |
| 11 | 13.75 | 31 | 6.75 | 51 | 2.25 |
| 12 | 13.50 | 32 | 6.50 | 52 | 2.00 |
| 13 | 13.00 | 33 | 6.25 | 53 | 1.75 |
| 14 | 12.50 | 34 | 6.00 | 54 | 1.50 |
| 15 | 12.00 | 35 | 5.50 | 55 | 1.50 |
| 16 | 11.75 | 36 | 5.25 | 56 | 1.50 |
| 17 | 11.50 | 37 | 5.00 | 57 | 1.25 |
| 18 | 11.00 | 38 | 4.75 | 58 | 1.25 |
| 19 | 10.50 | 39 | 4.50 | 59 | 1.00 |
| 20 | 10.00 | 40 | 4.50 | 60 | 1.00 |
| 21 | 9.50 | 41 | 4.25 | 61 | 1.00 |
| 22 | 9.25 | 42 | 4.00 | 62 | 0.75 |
| 23 | 9.00 | 43 | 4.00 | 63 | 0.75 |
| 24 | 8.75 | 44 | 3.75 | 64 | 0.50 |
| 25 | 8.50 | 45 | 3.50 | 65 | 0.50 |
| 26 | 8.00 | 46 | 3.25 | 66 | 0.50 |
| 27 | 7.75 | 47 | 3.00 | 67 | 0.25 |
| 28 | 7.50 | 48 | 2.75 | 68 | 0.25 |
| 29 | 7.25 | 49 | 2.50 | 69 | 0.00 |
| 30 | 7.00 | 50 | 2.50 | 70~ | 0.00 |

FIG. 15 (b)

| | |
|---|---|
| S-1 ····· | Decision of the vision value of the initial desired target upon measuring the vision of the previous spectacles. |
| S-2 ····· | To obtain the estimated vision value based on the residual degree obtained by the objective measuring d and the previous spectacles data from the tables E and F |
| S-3 ····· | Is there the actual data of the naked eye vision value ? |
| S-4 ····· | Is the estimated value of the naked eye vision value the same as the actual value ? |
| S-5 ····· | To perform the rectifying process based on the difference between the estimated value and the actual value of the naked eye vision values. |
| S-6 ····· | Is the rectifying value of the estimated value of the previous spectacles vision lower then the actual value of the naked eye vision ? |
| S-7 ····· | The estimated value of the previous spectacles. |
| S-8 ····· | The rectifying vision value of the previous spectacles. |
| S-9 ····· | The actual naked eye vision value. |

5,767,940

OPHTHALMIC APPARATUS

BACKGROUND OF THE INVENTION

1. Field of the Invention

The present invention relates to an ophthalmic apparatus, and more particularly to an ophthalmic apparatus suitable for adjusting a refractive corrected-power to correct defective in refraction of an eye to be examined, and for obtaining a prescribed power.

2. Description of Related Art

In the case that an eye to be examined shows defective in refraction and when it should be corrected, an examinee may inspects a refractive power of the examined eye, and prescribes a corrected power with no physical disorder and with satisfaction, in consideration of a power of a refractive power correcting tool such as spectacles or contact lens worn by the examinee.

As an ophthalmic apparatus for inspecting a refractive power of the examined eye, an eye-refractive power measuring apparatus is known, which measures objectively a refractive power of an eye based on a detection of a light bundle of a projected-target image transmitted from the fundus of the eye by means of photo-detecting elements by projecting a target for use in a measurement onto the fundus of the eye to be examined. Recently, this kind of apparatus has been capable of measuring high-accurately, and thereby a corrected value has been obtained that is almost close to a completely-corrected value of one obtained by a subjective inspection. Therefore, in the case of decision of a prescribed-power, it is commonly performed in a manner that a prescribed-power is decided by a temporary-frame inspection based on a data of objective value obtained by an eye-refractive power measuring apparatus, without performing a subjective inspection by a subjective ophthalmic device. In the temporary-frame inspection, a test lens, of which a refractive power is considered appropriate for the test, is mounted in the temporary-frame, and an inspection target is presented to the eye to be examined and thereby the power is adjusted, and then the prescribed-power is decided.

However, to desire an appropriate prescribed power by adjusting a power without over-correction under a temporary-frame inspection, greatly depends on knowledge and experience of an examiner, therefore the examiner who has little experience in the optometry holds hard to make an appropriate decision.

Additionally, to decide an appropriate prescribed power, it commonly takes much time and an individual difference among examiners is likely to occur.

On the other hand, in an eye-refractive power measuring apparatus for measuring objectively a refractive power of an eye to be examined, upon following an objective measurement, there are such cases that an unaided eye vision is inspected to obtain a reference information for use in decision of a prescribed value, and that a vision is inspected based on the data of the spectacles of the examinee-own, when the examinee has his own spectacles (in the following, it is called previous spectacles).

Upon these vision inspections, a vision value of a target, which is indicated at the beginning, is decided by the examiner in such a manner that the examinee expects an appropriate vision value by depending on an information such as condition-to-see and the like, which has been asked to the examinee.

Therefore, there is a case that at first an objective refractive power is obtained by using an eye-refractive power measuring apparatus, and then on the basis of the measuring data, an inspection target that should be indicated at first in an unaided eye vision inspection, is decided. Additionally, there is a case that a vision inspection by using previous spectacles is performed in a manner that a lens power of previous spectacles is measured at first, and then on the basis of the measuring data an inspection target that should be indicated at first, is decided.

However, a decision of an indicating target also greatly depends on experience and knowledge of the examiner, therefore the examiner unfamiliar to the inspection holds hard to decide the target. If the target is indicated, that is far apart from the original value of an unaided eye vision or the original value of previous spectacles vision, changes of inspection targets and decipherment and confirmation have to be performed over and over again, thereby the time for the inspection happens to be much longer.

In the case of hyperopia or astigmatism, the complicated judgement is needed, so the examiner unfamiliar to the inspection particularly holds hard to decide the inspection target.

SUMMARY OF THE INVENTION

The present invention has been made in view of the above circumstances and has an object to overcome the above problems and to provide an ophthalmic apparatus, which can easily and quickly desire the most appropriate prescribed-power.

Another object of the present invention is to provide an ophthalmic apparatus capable of giving an information of an eye to be examined, which is used in order to perform efficiently and accurately an unaided eye vision inspection or a previous spectacles vision inspection.

Additional objects and advantages of the present invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus for obtaining a refractive corrected power based on a refractive power which an eye to be examined has, the apparatus comprises input means for inputting data of objective values obtained by measuring objectively the refractive power of the eye to be examined and information of adjustment factors for adjusting a corrected power, program storing means for storing a program in order to adjust the corrected power against the data of objective values based on the data inputted by the input means and for expecting a prescribed power, executing means for executing the program stored in the program storing means, prescribed power calculating means for calculating an expected-prescribed power in response to the program executed by the executing means, and displaying means for displaying the expected-prescribed power calculated by the prescribed power calculating means.

In another aspect of the present invention, an ophthalmic apparatus for obtaining a refractive corrected power based on a refractive power which an eye to be examined has, the apparatus comprises objective refractive power measuring means for measuring objectively a refractive power of an eye based on projecting a target for a measurement onto a fundus of an eye to be examined and detecting a light bundle of a target image transmitted from a fundus of the eye by means of photo-detecting elements. subjective refractive power measuring means that has target indicating optical system which indicates a target for use in a subjective inspection and involves corrective optical system capable of adjusting a refractive power, for measuring a subjective refractive power of the eye to be examined on the basis of the adjustment by the corrective optical system, input means for inputting information of adjustment factors for adjusting a corrected power, program storing means for storing a program in order to adjust the corrected power against the data of the subjective value based on the data inputted by the input means and for expecting a prescribed power, executing means for executing the program stored in the program storing means, prescribed power calculating means for calculating an expected-prescribed power in response to the program executed by the executing means, and displaying means for displaying the expected-prescribed power calculated by the prescribed power calculating means.

According to an ophthalmic apparatus of the present invention, the most appropriate prescribed-power is obtained exactly and quickly.

Additionally, the apparatus of the present invention can inform an examiner of an information of an estimated value of an unaided eye vision based on an objective measuring data and an information of an estimated value of an unaided eye vision by a previous spectacles, therefore an examiner who has little experience can easily and efficiently perform an unaided eye vision inspection and a vision inspection by using a previous spectacles.

Furthermore, in the case of an apparatus which comprises a subjective inspecting mechanism for presenting an inspection target to the eye to be examined, the inspection is started from a target indication of an estimated vision, therefore even an examiner who has not skilled can efficiently perform an inspection.

BRIEF DESCRIPTION OF THE DRAWINGS

The present invention will be described with reference to the accompanying drawings, in which:

FIG. 3 is a view showing an example of an input screen, which is displayed at the monitor, at the time when the data-input-mode is selected;

FIG. 4(b) is a table for describing FIG. 4(a);

FIG. 5(b) is a table for describing FIG. 5(a);

FIG. 6(b) and FIG. 6(c) are tables for describing FIG. 6(a);

FIG. 7(b) and FIG. 7(c) are tables for describing FIG. 7(a);

FIGS. 8(b)–8(d) are tables for describing FIG. 8(a);

FIG. 9(b)–FIG. 9(d) are tables for describing FIG. 9(a);

FIG. 10(a)–FIG. 10(d) are views showing operation of table A to table D in order to obtain a rectifying-quantity for regulating a corrected power;

FIG. 11 is a view showing an example of an age input screen;

FIG. 14(a) and FIG. 14(b) are tables as standard for judgement to obtain an estimated value of a vision;

FIG. 15(a) is a flowchart for describing a routine procedure in decision of a visual acuity of an initial desired-target at the time of a previous spectacles measurement; and.

FIG. 15(b) is a table for describing FIG. 15(a).

DETAILED DESCRIPTION OF THE PREFERRED EMBODIMENTS

[The first preferred embodiment]

Figure 1:
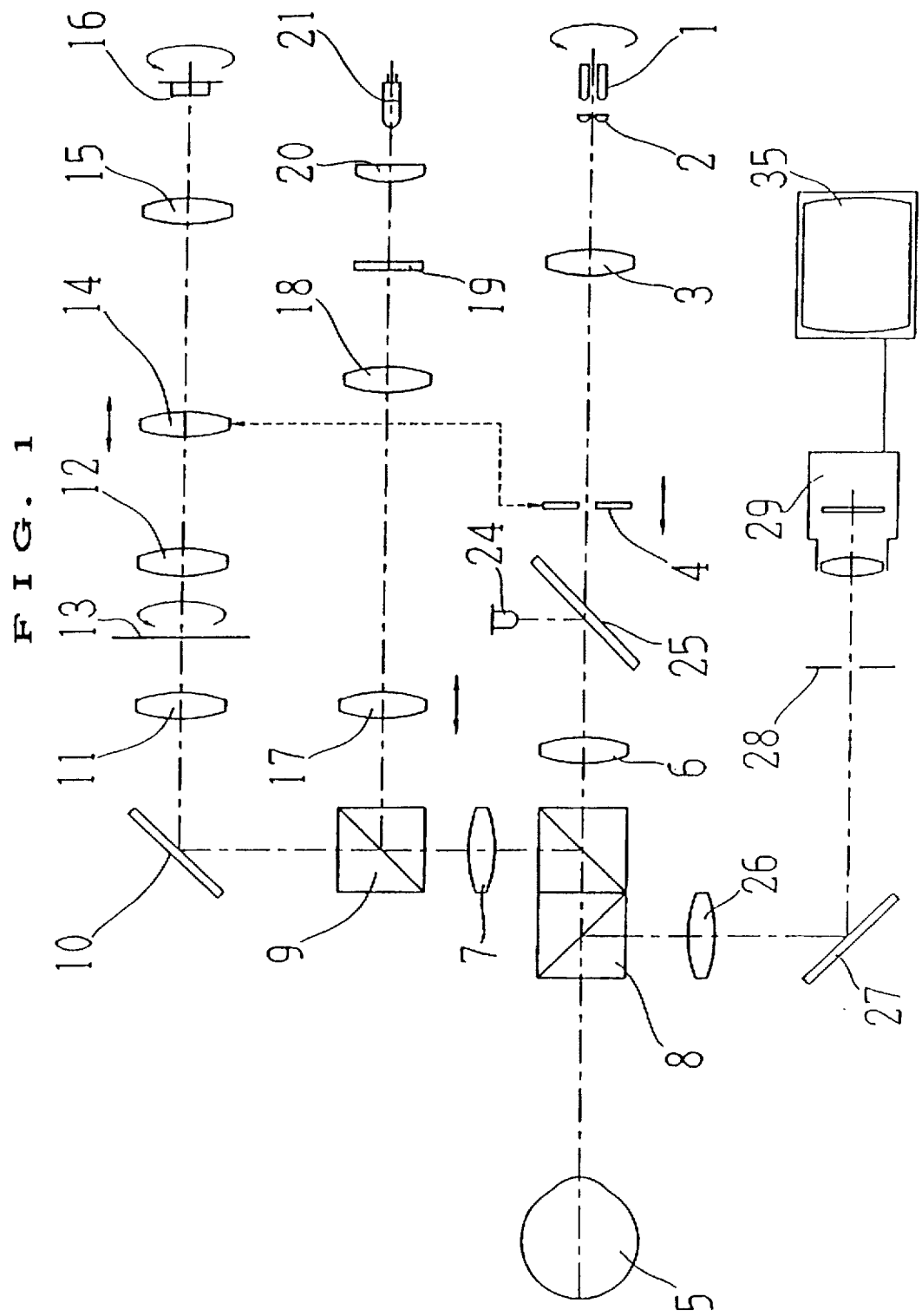
FIG. 1 is a view showing the optical system arrangement of a measuring apparatus for a refractive power of an eye according to the preferred embodiment of the present invention.

A detailed description of one preferred embodiment of an ophthalmic apparatus embodying the present invention will now be given referring to the accompanying drawings. FIG. 1 is a view showing an optical system arrangement of an eye-refractive power measuring apparatus of the first preferred embodiment.

(Objective refractive power measurement system)

Reference numeral is are a pair of measurement light sources having wavelength within a range of infrared-rays, and reference numeral 2 and 3 are condenser lenses. Reference numeral 4 is a measuring target plate, and moves so as to be disposed in a conjugate position against a fundus of an eye 5 to be examined. Reference numeral 6 is a projection lens for projecting a measurement-indicating-target onto a fundus of an examined eye, reference numeral 7 is an objective lens, and reference numeral 8 and 9 are beam splitters.

Reference numeral 10 is a reflecting mirror, and reference numeral 11 and 12 are relay lenses. Reference numeral 13 is a cornea reflection eliminating mask which is shaped like a belt, and is disposed in a conjugate position against a cornea of the eye 5, and can rotate about an optical axis as a center. Reference numeral 14 is a moving lens for moving together with the measurement target plate 14, and reference numeral 15 is a focusing lens. Reference numeral 16 is a photo-detecting element for measuring which is divided into 2, and rotates about the optical axis as a center being synchronized with the measurement light source 1 and the cornea reflection eliminating mask 13.

(Fixation target indicating system)

Reference numeral 17 is a first relay lens capable of moving on an optical axis, and the first relay lens 17 fogs the examined eye by moving on the optical axis. Reference numeral 18 is a second relay lens, reference numeral 19 is a fixation target which is placed in a focus position of the second relay lens 18, reference numeral 20 is a condenser lens, and reference numeral 21 is an illumination lamp.

(Alignment optical system and observation optical system)

Reference numeral 24 is a point light source for use in an alignment, which generates light within a range of infrared rays, and the point light source 24 is placed in a focus position of the objective lens 6 through a beam splitter 25. Light bundle emitted from the point light source 24 is reflected by the beam splitter 25, and then is made to be parallel light bundle by means of the projection lens 6, and thereby the alignment target is projected onto the cornea of the examined eye.

Light bundle transmitted from an anterior portion of the examined eye is reflected by the beam splitter 8, and then photographed by a CCD camera 29 through the objective lens 26, a reflecting mirror 27 and a telecentric diaphragm 28. The image of the anterior portion of the eye 5 and the image of the alignment target are projected on a monitor 35.

Figure 2:
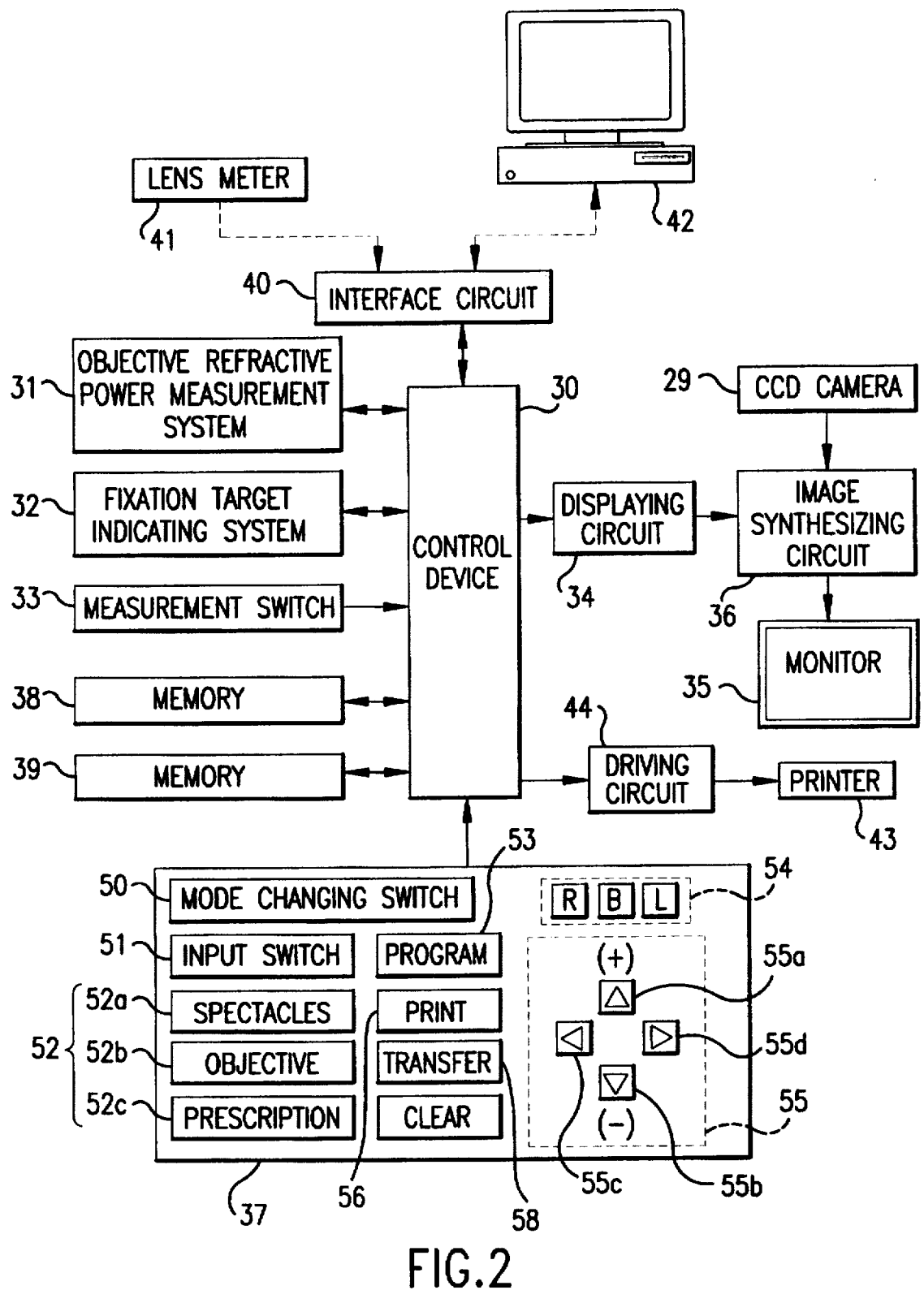
FIG. 2 is a block diagram showing an important part of control system according to the preferred embodiment of the present invention.

FIG. 2 is a view showing an important part of a control system according to the first preferred embodiment. Reference numeral 30 is a control device for controlling the operation of the whole apparatus, and makes an objective refractive power measurement system 31 and a fixation target indicating system go into run and thereby the objective refractive power measurement is performed. Additionally, the control device 30 calculates an adjustment power in response to an automatic adjustment program mentioned below. Reference numeral 33 is a measurement switch for generating a trigger signal to start the objective refractive power measurement. Reference numeral 34 is a displaying circuit for displaying various kinds of characters-information at the monitor 35, and the signal transmitted from the displaying circuit 34 is displayed at the monitor 35 through an image synthesizing circuit.

Reference numeral 37 is an input switch group provided with a mode changing switch 50 for changing a mode such as a measurement mode or some kinds of input modes or the like, an input switch 51 for inputting data of value of spectacles worn by the examinee (hereinafter which is also called previous spectacle value) and so on, an input designating switch group 52 for designating a kind of data at the time when a data is inputted, a program switch 53 for starting an automatic adjustment program (mentioned below), a selection switch 54 for selecting an examined eye, a direction switch group 55 which is used when degree items, displayed at the monitor, such as S (spherical power), C (astigmatism power), and A (astigmatism axial angle) are changed or modified, and a print switch 56.

Reference numeral 38 is a memory stored therein automatic adjustment programs and control programs, and reference numeral 39 is a memory for storing therein some kinds of data. Reference numeral 40 is an interface circuit for performing input/output of data, and a lens meter 41 for measuring a refractive power of a spectacles lens or a contact lens is connected with the principal apparatus by using a cable through the interface circuit 40, and thereby the measuring data measured by the lens meter 41 can be transferred and inputted. Additionally, the data stored in the memory 39 can be transferred and outputted to external devices such as a host computer 42 or the like through the interface circuit 40. An input/output of data to the lens meter 41 or to another ophthalmic apparatus can be also performed by using an IC card and an IC card-read-writer. Reference numeral 43 is a printer and reference numeral 44 is its driving circuit.

The operation of the apparatus having such architecture as described above will be described. Hereinafter, such operation will be described that an objective refractive power measurement is performed and then an automatic adjustment program is executed and thereby a standard power for prescription is calculated.

(A) Objective refractive measurement

In the case that the objective refractive power measurement is performed, the mode is changed to an objective refractive power measurement mode by using the mode changing switch 50, and the examined eye is positioned at the predetermined position. Then the examined eye, which is positioned at measurement side, is selected by using the right/left selection switch 54. The examiner aligns the device with the examined eye so as to be the predetermined positional relation, with his eye observing the anterior portion image of the examined eye and the alignment target image, which are projected onto the monitor 35 transmitted through the observation optical system, and the aim mark which is generated by the displaying circuit, and then when the examiner depresses the measurement switch 33, the measurement is started and performed.

The infrared rays irradiated from the measurement light source 1 is transmitted through the condenser lenses 2 and 3, the measurement target 4, the projection lens 6 and the beam splitter 8, and then after the rays is condensed into around the cornea of the eye 5, it reaches to the fundus of the eye. The examined eye is made to fix to the fixation target which is illuminated by the illumination lamp 21. In the case that the examined eye is normal, the target image reflected by the fundus of the eye is transmitted through the beam splitters 8 and 9, and is reflected by the reflecting mirror 10, and is also transmitted through the relay lenses 11 and 12, then the target image is focused onto the photo-detecting elements 16 by the focusing lens 15. In the case that refractive ametropia exists, the control device 30 makes the measurement target 4 together with the moving lens 14 move so that the measurement target 4 may be at the conjugate position against the fundus of the eye 5.

Successively, the control device 30 moves the first relay lens 17 so that the position of the fixation target may be at conjugate position against the fundus of the eye, and then further moves the first relay lens 17 so that the fogging may be attached to an appropriate quantity of diopter. Under the condition that the fogging is attached to the examined eye, the measurement light source 1, cornea reflection eliminating mask 13 and the photo-detecting element for measuring 16 are made to rotate with being synchronized with each other. While the rotation, the value of the refractive power of the eye 5 against respective meridians can be known by a photo-detecting signal transmitted from the photo-detecting element 16 for measuring, and the control device 30 obtains respective data of the objective values of S-value (spherical power), C-value (astigmatism power) and A-value (astigmatism axial angle) by performing the predetermined process about the value of the refractive power every respective meridians.

After the measurement of one eye has accomplished, the measurement of another eye is performed in the same way, and thereby the data of objective values for both eyes are obtained. The obtained data of the objective values are stored in the memory 39.

(B) Data input

When the examinee wears his pair of spectacles, a power of the spectacles is measured by the lens meter 41. The data of previous spectacles value is transferred through the interface circuit 40 and stored into the memory 39 by depressing the print switch of the lens meter 41.

The data of previous spectacles value can be inputted manually by a switching operation as well as an input by a data-communication. In this case, the operation is performed as in the following. The data-input-mode is selected by operating the mode changing switch 50. At the monitor 35, an input screen designated by FIG. 3 is displayed. When the spectacles-switch 52a of the input designating switch group 52 is depressed, a section of "LM" which means the data of previous spectacles value in the upper row is reversely displayed, and further the numerical part of S-value for the right eye is reversely displayed. The mode which the numerical value of the part displayed reversely can be inputted, is set in. The numerical value which should be inputted is alternated by depressing an upper-direction switch 55a and a lower-direction switch 55b in a direction switch group 55. The numeric can be increased by the predetermined diopter step (in the preferred embodiment, the power step is defined as 0.25D step) every time when the upper-direction switch 55a is depressed, and can be decreased by 0.25D step every time when the lower-direction switch 55b is depressed. C-value and A-value of which the numerical value part displayed reversely is successively changed to the right for one item by depressing the right-direction switch 55d, and the numerical value which should be inputted can be alternated by depressing the upper-direction switch 55a and the lower-direction switch 55b. When the data of left eye is inputted, a L switch in the selection switch 54 is depressed, and as the same way, the numerical value about respective items are inputted by operating the direction switch group 55. All of the input operation have completed, the data inputted on the screen are stored in the memory 39 by depressing the data input switch 51.

Still, in the case that the data of objective value is stored in the memory 39, if the mode is changed to the data-input-mode by using the mode changing switch 50, the stored data is displayed at the section of "AR" which means the data of objective value. Additionally, this data of objective value can be manually inputted. If the objective switch 52b in the input designating switch group 52 is depressed, the section of "AR" comes to being displayed reversely, therefore the numerical value about the respective power items is inputted. And then, by depressing the data input switch 51, the data inputted on the screen is stored in the memory 39.

(C) Calculation of the standard power which is expected of the prescribed value

When the data of objective value and the data of previous spectacles value have inputted (if there is not a data of previous spectacles value, it is regarded as the examinee is initial wear), the program switch 53 is depressed. If this switch signal is inputted, the control device 30 calculates the prescribed value which is expected that most suitable for the examinee in response to the automatic adjustment program stored in the memory 38. The standard power of the calculated prescribed power is displayed at the section of "FINAL" (which means the prescribed power) in the input screen. The automatic adjustment program will be described below with reference to the flowcharts shown in FIG. 4 to FIG. 9. Still, "power-strong eye" means the larger one between the absolute values for respective S-values or C-values, and "power-weak eye" means reverse of it, in the following description. Additionally, the astigmatism (C-value) is read in a manner of minus-reading.

Figure 4A:
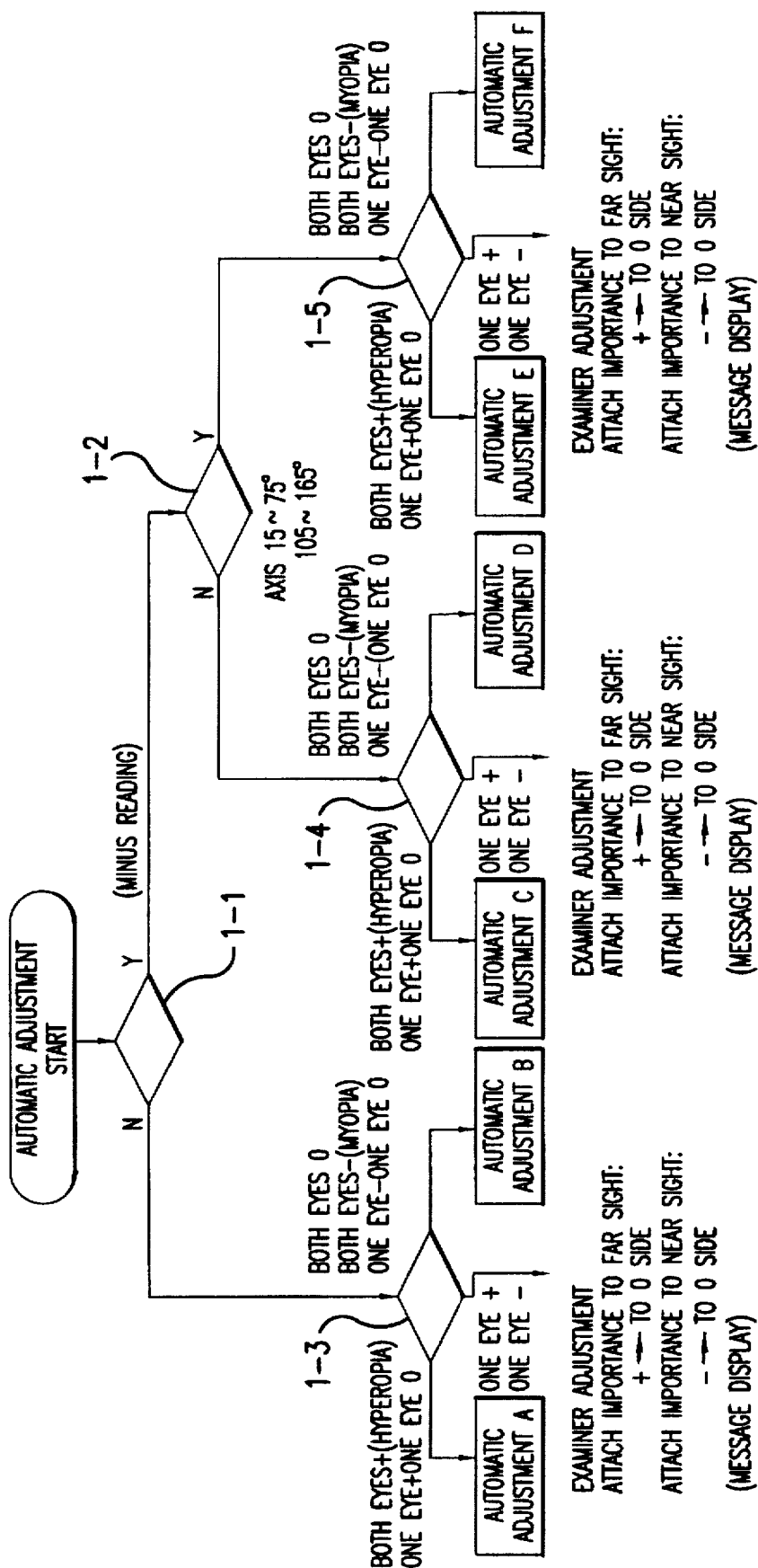
FIG. 4(a) is a flowchart for describing a routine procedure in an automatic adjustment program.

As shown in FIG. 4, the control device 30 judges based on the data of objective values whether astigmatism exists or not (Step 1-1). In the case that astigmatism exists, further it is judged whether oblique astigmatism exists or not(axis: within a range from 15° to 75° or a range from 105° to 165°). After that, according to the S-value of both eyes it is judged whether hyperopia (both eyes are plus, or one eye is plus and another is 0) exists or myopia (both eyes are minus, or one eye is minus and another eye is plus) exists, and thereby any of the automatic adjustment A through F is performed and the adjustment power is calculated. In the case that it can not be distinguished between hyperopia from myopia (in the case that the S-value of one eye is plus and the S-value of another eye is minus), the power adjustment can not be performed and the message which means that the examiner adjusts is displayed.

[Automatic adjustment A: Astigmatism does not exist, and the case is hyperopia]

Figure 5A:
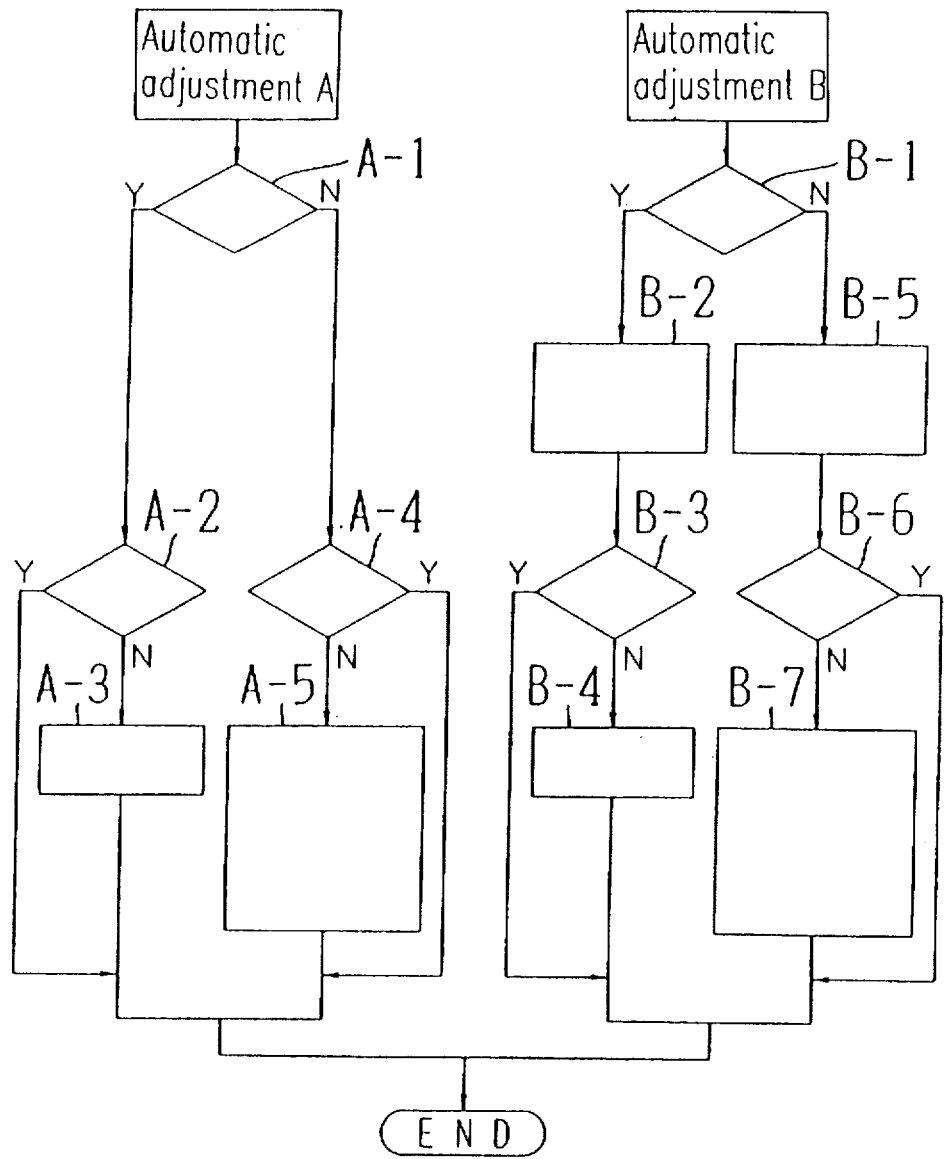
FIG. 5(a) is a flowchart for describing a routine procedure in an automatic adjustment program.

As shown in FIG. 5, the apparatus judges whether the examinee is in initial spectacles wear or not (Step A-1), based on existence of input-operation of the data of previous spectacles value (existence of experience of spectacles wear). [A-1] Next, in the case of initial spectacles wear, the difference in S-values between right eye and left eye is compared (Step A-2). If the difference in S-values between right eye and left eye is less than or equal to the predetermined power-difference, the adjustment power is defined as the objective value, kept as it is. In the case that the difference in S-values between right eye and left eye is greater than 0.75D, the S-value of power-strong eye is adjusted to a power obtained by adding +0.75D to the S-value of power-weak eye (Step A-3). [A-2] Not in the case of initial spectacles wear, the difference in S-values between right eye and left eye is compared (Step A-4), and when it results in the case that the difference between right and left is greater than 0.75D, the S-value of power-strong eye side is adjusted so as not to be greater than the objective value by obtaining the larger one between a value obtained by adding +0.75D to the S-value of power-weak eye and a value obtained by adding the predetermined power (in the case of hyperopia, it is defined as less than or equal to +0.75D) to the S-value of the same side of the previous spectacles.

[Automatic adjustment B: The case of myopia exclusive of astigmatism]

[B-1] It is judged whether the initial spectacles wear is performed by the examinee or not (Step B-1). In the case of the initial spectacles wear, at first, the rectifying quantity Δ S1 is obtained based on an objective S-value of power-weak eye as reference by arithmetic process shown in table A of FIG. 10(a), and then the rectifying process (in the following, it is regarded as a rectifying process A1) for respectively subtracting the rectifying quantity Δ S1 from the objective S-values on both eyes is performed (Step B-2). Next, the difference between right eye and left eye after the rectifying process is compared (Step B-3), and thereby, in the case that the difference is greater than 0.75D, the S-value of power-strong eye side is adjusted to a value obtained by adding −0.75D to the S-value of power-weak eye (Step B-4).

[B-2] Not in the case of the initial spectacles wear, the rectifying quantity Δ S2 is obtained based on the smaller one between right eye and left eye about the difference between the previous spectacles and objective value as reference by arithmetic process shown in table B of FIG. 10(b), and then the rectifying process (in the following, it is regarded as a rectifying process B1) for respectively subtracting the rectifying quantity Δ S2 from the objective S-values on both eyes is performed (Step B-5). Next, the difference in S-value between right eye and left eye after the rectifying process is compared (Step B-6), and thereby, in the case that the difference is greater than 0.75D, the S-value of power-strong eye side is adjusted so as not to be greater than the objective value by obtaining the larger one between the absolute value obtained by adding −0.75D to the S-value of power-weak eye which is processed by the rectifying process and the absolute value obtained by adding the predetermined power (in the case of myopia, it is defined as less than or equal to −0.75D) to the S-value of previous spectacles (Step B-7).

[Automatic adjustment C: The case of hyperopia having astigmatism exclusive of oblique astigmatism]

Figure 6A:
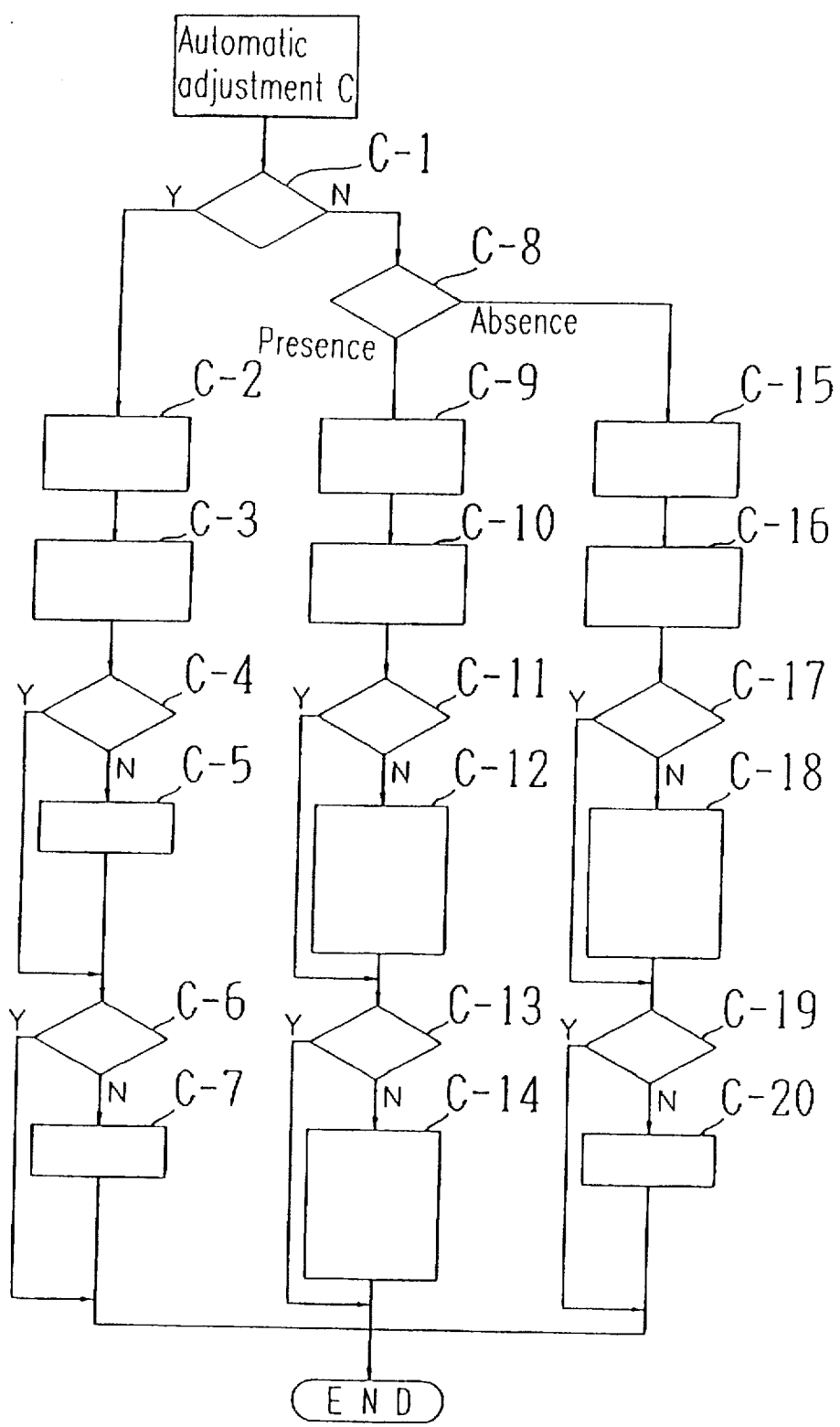
FIG. 6(a) is a flowchart for describing a routine procedure in an automatic adjustment program.

[C-1] As shown in FIG. 6, it is judged that the examinee is in initial spectacles wear or not (Step C-1). In the case of initial spectacles wear, at first, the rectifying quantity $\Delta$ C1 is obtained based on the value of power-weak eye of the C-value as reference by arithmetic process shown in table C of FIG. 10(c), and then the rectifying process (in the following, it is regarded as a rectifying process C1) for respectively subtracting the rectifying quantity $\Delta$ C1 from the objective C-values on both eyes is performed (Step C-2). Successively, the each of S-values of both eyes is adjusted to a value leading to an equivalent spherical surface by adding a half of rectifying quantity $\Delta$ C to a binocular completely-corrected value (Step C-3). Thereafter, the difference in obtained-S-value between right and left is compared (Step C-4), and thereby, in the case that it is greater than 0.75D, the S-value of power-strong eye side is adjusted to a value obtained by adding +0.75D to the S-value of power-weak eye (Step C-5). Next, the difference in C-value between right eye and left eye after the rectifying process C1 is compared (Step C-6), and thereby, in the case that the difference is greater than 0.75D, the C-value of power-strong eye is adjusted to a value obtained by adding −0.75D to the C-value of power-weak (Step C-7).

[C-2] Not in the case of the initial spectacles wear, at first, the judgement about the existence of astigmatism in the previous spectacles value is performed (Step C-8). When astigmatism exists in the previous spectacles value, the rectifying quantity $\Delta$ C2 is obtained based on the smaller one between the right eye and the left eye about the difference between the previous spectacles and objective value as reference by arithmetic process shown in table D of FIG. 10(d), and then the rectifying process (in the following, it is regarded as a rectifying process D1) for respectively subtracting the rectifying quantity $\Delta$ C2 from the objective C-values on both eyes is performed (Step C-9). Successively, the each of S-values of both eyes is adjusted to a value leading to an equivalent spherical surface by adding a half of rectifying quantity $\Delta$ C2 to a binocular completely-corrected value (Step C-10). Thereafter, the difference in obtained-S-value between right and left is compared (Step C-11), and thereby, in the case that it is greater than 0.75D, the S-value of power-strong eye side is adjusted so as not to be greater than the objective value by obtaining the larger one between the absolute value obtained by adding −0.75D to the S-value of power-weak eye which is lead to equivalent spherical surface and the absolute value obtained by adding +0.75D to the S-value of the same side of the previous spectacles value (Step C-12). Next, the difference in C-value between right eye and left eye after the rectifying process D1 is greater than 0.75D (Step C-13), the C-value of power-strong eye side is adjusted so as not to be greater than the objective value by obtaining the larger one between the absolute value obtained by adding −0.75D to the C-value of power-weak eye and the absolute value obtained by adding −0.75D to the C-value of the same side of previous spectacles (Step C-14).

When the judgement about the existence of astigmatism in the previous spectacles power results in that astigmatism is not exists (Step C-8), the rectifying process is performed (Step C-15), and successively, the each of S-values of both eyes is adjusted to a value leading to an equivalent spherical surface by adding a half of rectifying quantity $\Delta$ C1 to a binocular completely-corrected value (Step C-16). Thereafter, the difference in obtained-S-value between right and left is compared (Step C-17), and thereby, in the case that it is greater than 0.75D, the S-value of power-strong eye side is adjusted so as not to be greater than the objective value by obtaining the larger one between the absolute value obtained by adding +0.75D to the S-value of power-weak eye which is lead to equivalent spherical surface and the absolute value obtained by adding +0.75D to the S-value of the same side of the previous spectacles value (Step C-18). Next, the difference in C-value between right eye and left eye after the rectifying process C1 is compared (Step C-19), and thereby, in the case that the difference is greater than 0.75D, the C-value of power-strong eye is adjusted to a value obtained by adding −0.75D to the C-value of power-weak eye (Step C-20)

[Automatic adjustment D The case of myopia having the astigmatism exclusive of the oblique astigmatism]

Figure 7A:
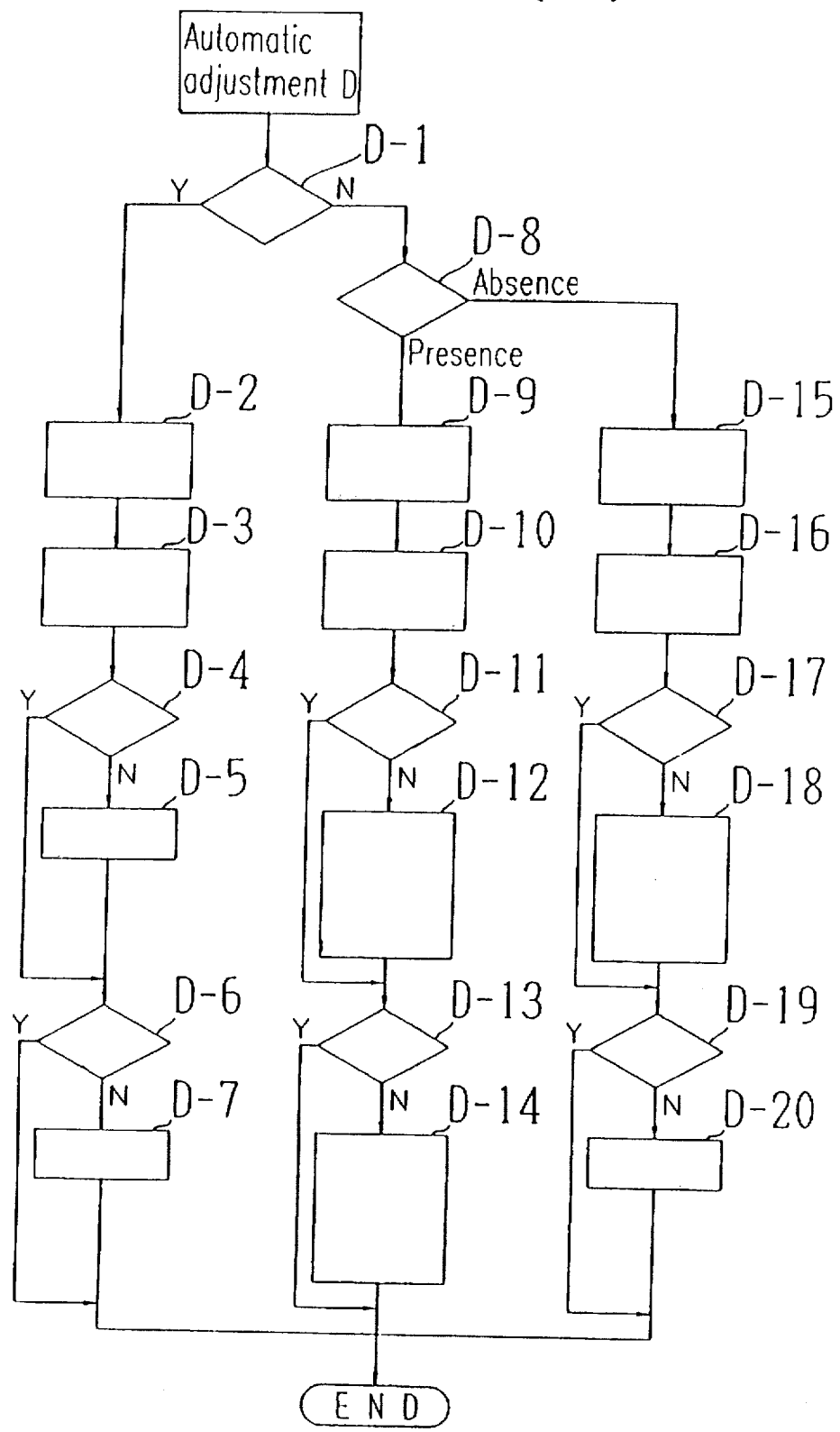
FIG. 7(a) is a flowchart for describing a routine procedure in an automatic adjustment program.

[D-1] As shown in FIG. 7, it is judged that the examinee is in initial spectacles wear or not (Step D-1). In the case of initial spectacles wear, the rectifying process C1 (Step D-2) and the rectifying process A1 (Step D-3) are successively performed. Thereafter, the difference in obtained-S-value between right and left is compared (Step D-4), and thereby, in the case that it is greater than 0.75D, the S-value of power-strong eye side is adjusted to a value obtained by adding −0.75D to the S-value of power-weak eye (Step D-5). Next, the difference in C-value between right eye and left eye after the rectifying process C1 is compared (Step D-6), and thereby, in the case that the difference is greater than 0.75D, the C-value of power-strong eye is adjusted to a value obtained by adding −0.75D to the C-value of power-weak (Step D-7).

Not in the case of the initial spectacle wear, at first, the judgement about the existence of astigmatism in the previous spectacles value (Step D-8). In the case that the astigmatism exists, the rectifying process D1 is performed (Step D-9). Successively, the rectifying process B1 is performed (Step D-10). Thereafter, the difference in obtained-S-value between right and left is compared (Step D-11), and thereby, in the case that it is greater than 0.75D, the S-value of power-strong eye side is adjusted so as not to be greater than the objective value by obtaining the larger one between the absolute value obtained by adding −0.75D to the S-value of power-weak eye and the absolute value obtained by adding −0.75D to the S-value of the same side of the previous spectacles value (Step D-12). Next, the difference in C-value between right eye and left eye after the rectifying process D1 is compared (Step D-13), and thereby, in the case that the difference is greater than 0.75D, the C-value of power-strong eye is adjusted so as not to be greater than the objective value by obtaining the larger one between the absolute value obtained by adding −0.75D to the C-value of power-weak eye and the absolute value obtained by adding −0.75D to the C-value of the same side of the previous spectacles (Step D-14).

When the judgement about the existence of astigmatism in the previous spectacles power results in that astigmatism is not exists, the rectifying process C1 and the rectifying process B1 are performed (Step D-15, D-16). Thereafter, the difference in obtained-S-value between right and left is compared (Step D-17), and thereby, in the case that it is greater than 0.75D, the S-value of power-strong eye side is adjusted so as not to be greater than the objective value by obtaining the larger one between the absolute value obtained by adding −0.75D to the S-value of power-weak eye and the absolute value obtained by adding −0.75D to the S-value of the same side of the previous spectacles value (Step D-18). Next, the difference in C-value between right eye and left eye after the rectifying process C1 is compared, and thereby, in the case that the difference is greater than 0.75D, the C-value of power-strong eye is adjusted to a value obtained by adding −0.75D to the C-value of power-weak eye (Step D-19, D-20).

[Automatic adjustment E: The case of hyperopia having the astigmatism inclusive of the oblique astigmatism]

Figure 8A:
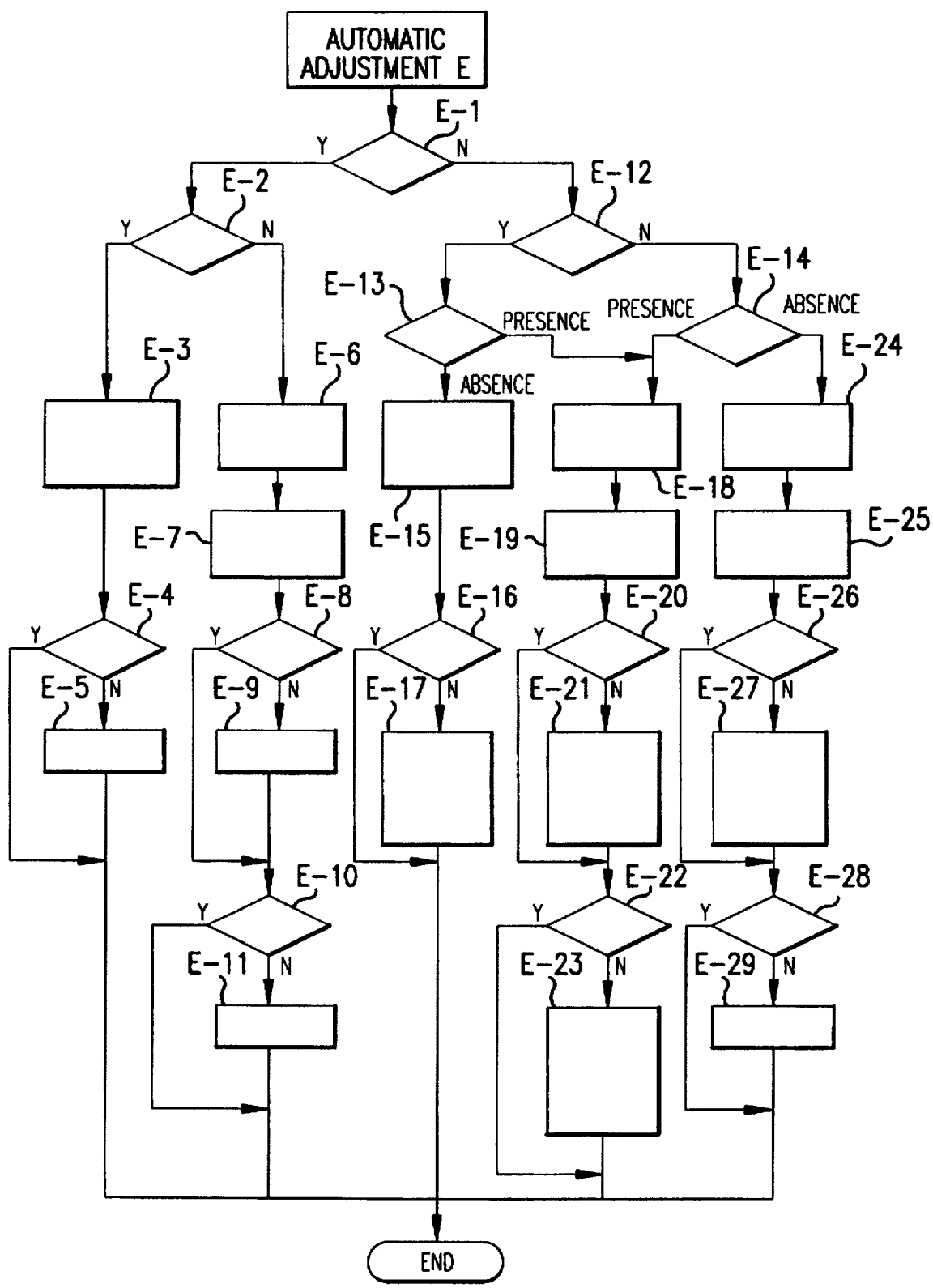
FIG. 8(a) is a flowchart for describing a routine procedure in an automatic adjustment program.

[E-1] As shown in FIG. 8, it is judged that the examinee is in initial spectacles wear or not (Step E-1). In the case of initial spectacles wear, next, the C-values both of right eye and left eye are less than or equal to −0.50D (as described below, in the preferred specification, C-value which is less than or equal to −0.50 designates the smaller one of the powers, in other words, is designates −0.25D or −0.50D) (Step E-2). In the case of the oblique astigmatism, when the C-value is small, it happens to be more preferable that the correction of astigmatism is not performed, so in the case that the C-values are less than or equal to −0.5D, the C-value is adjusted to 0 by regarding the astigmatism as to be ignored, and the S-values of right eye and left eye are adjusted to the equivalent spherical surface obtained by adding each of the half of C-values (Step E-3). Thereafter, the difference in obtained-S-value between right and left is compared (Step E-4), and thereby, in the case that it is greater than 0.75D, the S-value of power-strong eye side is adjusted to a value obtained by adding +0.75D to the S-value of power-weak eye (Step E-5).

In the case that it is judged whether the C-value is less than or equal to −0.5D (Step E-2), when the C-value of at least one of the right and left is greater than −0.5D, the rectifying process C1 is performed (Step E-6), the each of S-values of both eyes is adjusted to a value leading to an equivalent spherical surface by adding a half of rectifying quantity Δ C1 to the objective value (Step E-7). Next, in the case that the difference in C-value between right eye and left eye after the rectifying process C1 is greater than 0.75D, the C-value of power-strong eye is adjusted to a value obtained by adding −0.75D to the C-value of power-weak (Step E-10, E-11).

[E-2] In the case that the examinee is not in the initial spectacles wear, at first, it is judged whether the C-values both of right eye and left eye are less than or equal to −0.50D (Step E-12), and then it is judged that the each of previous spectacles value has astigmatism or not (Step E-13, E-14). In the case that each of the objective C-value is within −0.5D and the previous spectacles does not have astigmatism, the C-value is adjusted to 0 and the S-values of right eye and left eye are adjusted to values leading to equivalent spherical surface obtained by adding respectively a half of C-values (Step E-15). Thereafter, the difference in obtained-S-value between right and left is compared (Step E-16), and thereby, in the case that it is greater than 0.75D, the S-value of power-strong eye side is adjusted so as not to be greater than the objective value by obtaining the larger one between the absolute value obtained by adding +0.75D to the S-value of power-weak eye leading to equivalent spherical surface and the absolute value obtained by adding +0.75D to the same side of the S-value of previous spectacles (Step E-17).

No matter what the objective C-value is, the previous spectacles has astigmatism, the same process as from the Step C-9 to C-14 (Step E-18 to 23).

In the case that the C-value of at least one of light eye and left eye is greater than −0.5D and the previous spectacles does not have astigmatism, the rectifying process C1 is performed (Step E-24), the S-values of both eyes are adjusted to values leading to equivalent spherical surface obtained by adding a half of the rectifying quantity Δ C1 to the objective value (Step E-25). Successively, the difference in obtained-S-value between right and left is compared (Step E-26), and thereby, in the case that the difference is greater than 0.75D, the same process as the Step C-11 is performed (Step E-27). Next, the difference in C-value between right eye and left eye after the rectifying process C1 is compared (Step E-28), and thereby, the difference between right and left is greater than 0.75D, the C-value of power-strong eye is adjusted to a value obtained by adding −0.75D to the C-value of power-weak eye (Step E-29).

[Automatic adjustment F: The case of myopia having the oblique astigmatism]

Figure 9A:
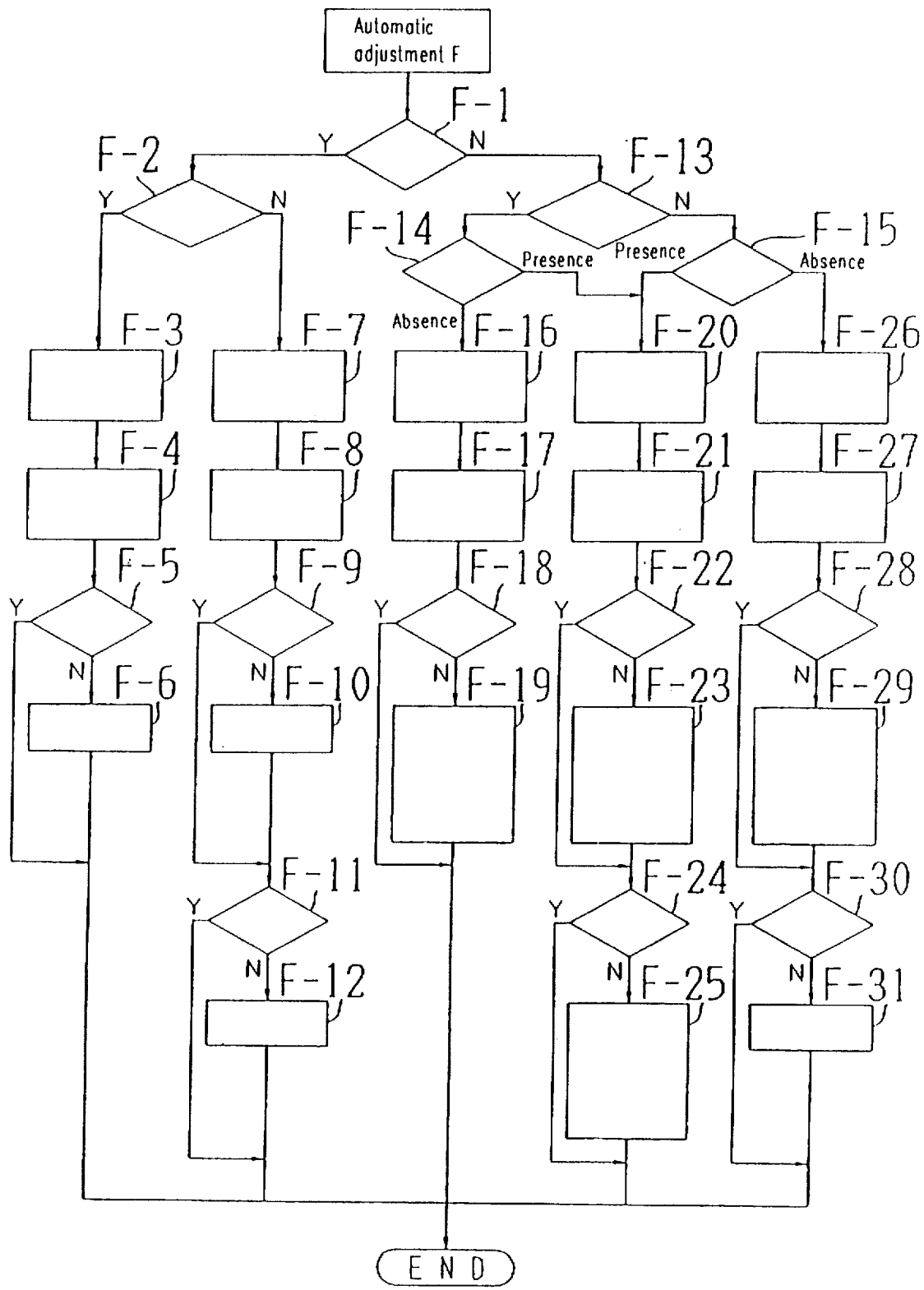
FIG. 9(a) is a flowchart for describing a routine procedure in an automatic adjustment program.

[F-1] As shown in FIG. 9, it is judged that the examinee is in initial spectacles wear or not (Step F-1). In the case of initial spectacles wear, next, it is judged whether the C-values both of right eye and left eye are less than or equal to −0.50D (Step F-2). When the both C-values are within −0.5D, the both C-values are adjusted to 0 (Step F-3). Successively, rectifying process A1 is performed about the S-value (Step F-4). Thereafter, the difference in obtained-S-value between right and left is compared (Step F-5), and thereby, in the case that the difference between right and left is greater than 0.75D, the S-value of the power-strong eye is adjusted to a value obtained by adding −0.75D to the S-value of power-weak eye (Step F-6).

In the case that it is judged whether the C-value is less than or equal to −0.5D (Step F-2), when at least one of right and left is greater than −0.5D, the rectifying process C1 is performed (Step F-7). Successively, the rectifying process A1 is performed about the S-value (Step F-8). Thereafter, the difference in obtained-S-value between right and left is compared (Step F-9), and thereby, in the case that the difference between right and left is greater than 0.75D, the S-value of the power-strong eye side is adjusted to a value obtained by adding −0.75D to the S-value of power-weak eye (Step F-10). Next, the difference in C-value between right and left eye after the rectifying process C1 is compared (Step D-11), and thereby, in the case that the difference between right and left is greater than 0.75D, the C-value of power-strong eye is adjusted to a value obtained by adding −0.75D to the C-value of power-weak eye (Step F-12).

[F-2] In the case that the examinee is not in the initial spectacles wear, at first, it is judged whether the both C-values of right and left are less than or equal to −0.50D (Step F-13), and then it is judged that the respective previous spectacles values have astigmatism or not (Step F-14, F-15).

In the case that the objective C-value is within −0.5D and the previous spectacles does not have astigmatism, the C-value is adjusted to 0 (Step F-16). Successively, the rectifying process B1 is processed (Step F-17). Thereafter, the difference in obtained-S-value between right and left is compared (Step F-18), and thereby, in the case that the difference between right and left is greater than 0.75D, the S-value of power-strong eye side is processed by the same process as Step B-17 (Step F-19).

In the case that the previous spectacles have astigmatism no matter what the objective C-value is, the same process as from Step D-9 to Step D-14 (Step F-20 to F-25).

In the case that the C-value of at least one of light and left is greater than −0.5D, the rectifying process C1 is performed about the C-value (Step F-26), and the rectifying process B1 is performed about the S-value (Step F-27). Thereafter, the difference in obtained-S-value between right and left is compared (Step F-28), and thereby, in the case that the difference between right and left is greater than 0.75D, the same process as the Step B-7 is performed about the S-value of power-strong eye (Step F-29). Next, the difference in C-value between right and left after the rectifying process C1 is compared (Step F-30), and thereby, the difference between right and left is greater than 0.75D, the C-value of power-strong eye is adjusted to a value obtained by adding −0.75D to the C-value of power-weak eye (Step F-31).

When the apparatus can distinguish hyperopia from myopia as described above, the one of the processes among the automatic adjustment A to F is performed, and thereby the standard power of prescribed value is automatically calculated and the value is displayed at the monitor 35.

Additionally, in above mentioned automatic adjustment programs, in the case that the changed-quantity from the previous spectacles of the same side is adopted <as an adjustment quantity>, the adjustment quantity for adjusting the S-value or C-value of power-strong eye side is adjusted to a value obtained by adding ±0.75D (3 grades) to the S-value or C-value (Step A-5, B-7, C-14 or the like), however according to the age of an examinee, it is also considered that an adjustment quantity of ±0.50D (2 grades) can be changed. It is caused by that the adopting-ability against the power-change of the previous spectacles is different in ages. The young people can adopt himself even if there is the change of 3 grades (0.75D), however in general, the change of about 2 grades (0.50D) is a limit for the old people. Therefore, if the adjustment quantity of prescribed power should be changed in response to the adopting-ability of the examined eye, the prescription can be more suitable for the person wearing his spectacles.

Figure 11:
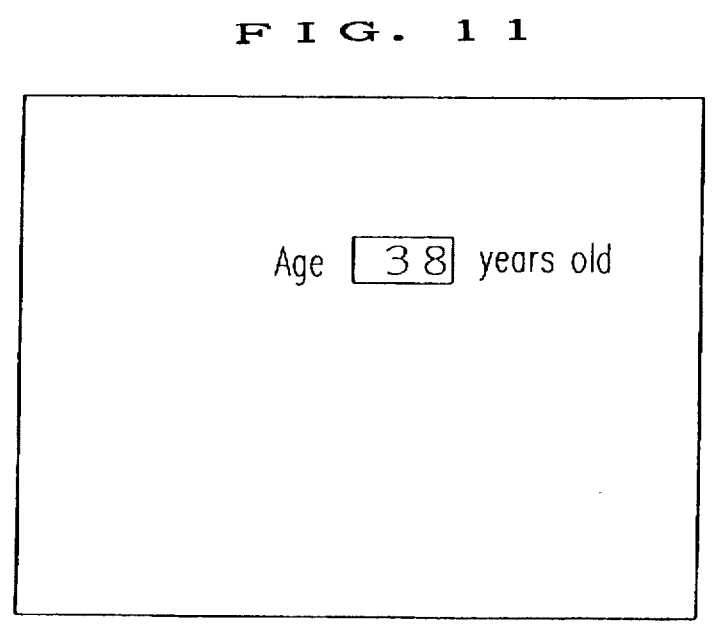

In the case that the adjustment quantity of power is should be changed, it is performed as the following. In the automatic program, for example, the 2 kinds of adjustment quantity of power, which is 3 grades (0.75D) and 2 grade (0.50D), are prepared according to whether the examinee is older than a certain age (38 years old) or not (further, it is considered that many switches are provided). In case of the input of age of examinee, at first, the mode is changed to the age-input-mode by depressing the mode changing switch 50 and the age input screen is made to displayed at the monitor 35 (which see FIG. 11). And then, the age can be made to input by depressing the upper-direction switch 55a and the lower-direction switch 55b. The apparatus calculates the standard power by using the adjustment quantity which is described above and determined in advance, in response to the signal of the inputted-age. Also, quantity of power adjustment can be changed by inputting an information obtained in a manner that the examiner himself judges whether the adopting-ability is high or low.

Additionally, in the objective refractive power measurement, since the far viewing refractive power of 5 meters is obtained, it is regarded that the standard power which is expected most suitable for the distance of 5 meters in above mentioned automatic adjustment program, however by inputting the distance which is used by the examinee, it is rectified to the power suitable for the distance inputting the standard power of prescribed value. The distance used by the examinee is inputted by depressing the mode changing switch 50 and then selecting the input mode for the distance and thereby making display the distance input screen at the monitor 35. If the using-distance is changed by the input, the apparatus rectifies the calculated-power in response to the input distance, directly before the automatic adjustment program is executed based on the input signal. For example, if the distance of infinite far is inputted against the power of the far viewing distance of 5 meters, rectification by adding −0.25D to the S-value is performed, and if the distance of 2 meters is inputted, rectification by adding +0.25D to the S-value is performed.

(D) Temporary-frame inspection

The examiner mounts the test lens in the temporary-frame and presents the inspection-target to the examined eye through the test lens. In the temporary-frame inspection, it is needed that only fine-adjustment for physical disorder and condition-to-see based on the expected power a test lens is performed, therefore the prescribed power is determined in a short time without over-correction.

After the prescribed value adjusted finely is decided, a value of the section of "FINAL" is changed and inputted. This is performed as the following. When the prescribed switch 52c in the input designating switch group 52 is depressed, the section of "FINAL" shown in FIG. 3 is reversely displayed. In the beginning, the S-value for use in right eye is reversely displayed, and the mode comes to a mode capable of changing and inputting the numerical value which is reversely displayed. Respective values of S, C, A are capable of being inputted and changed by operating the direction switch group 55, and the change of another eye is performed by using the selecting switch 54. After the change and the input has completed, the respective changed values are stored in the memory 39 by depressing the input switch 51.

The final prescribed value is printed out from the printer 54 by depressing the print switch 57. The result which is printed out can be used for making spectacles for use in a correcting tool.

Additionally, the prescribed value, the data of objective value and the data of previous spectacles value are transferred into the host computer 42 by depressing the transfer switch 58, and thereby the stored data can be used for various kinds of data control in the host computer 42.

As described above, the first preferred embodiment is described by applying the eye-refractive power measuring apparatus for measuring objectively the refractive power of the examined eye, however other construction is also considered that the estimated prescribed-power is calculated by executing the automatic adjustment program by inputting manually (or input by communication data transfer) the data of objective value obtained by using another apparatus or the like.

Additionally, the automatic adjustment program can calculates a half of a sum of the data of objective value and the data of the spectacles value as a prescribed value.

[The second preferred embodiment]

Figure 12:
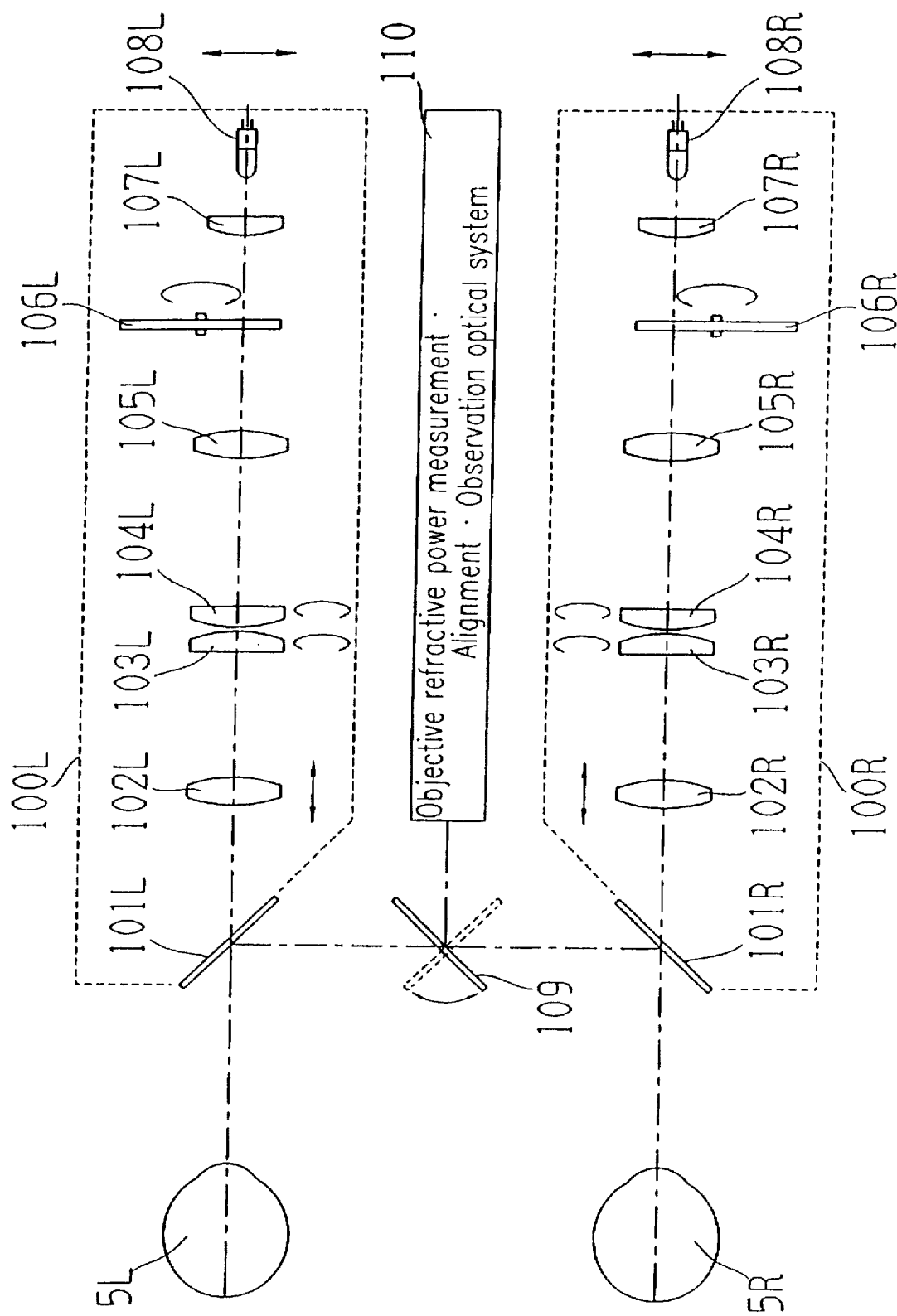
FIG. 12 is a view showing a schematic arrangement of an optical system according to the second preferred embodiment of the present invention.

The apparatus of the second preferred embodiment is an example of the eye-refractive power measuring apparatus having a subjective inspection function against the first preferred embodiment. The schematic arrangement of an optical system according to the second preferred embodiment will be described referring to FIG. 12.

[The target indicating optical system]

The target indicating optical system is constructed with a target indicating optical system 100R for right eye 5R and a target indicating optical system 100L for left eye 5L. The target indicating optical system 100R has such architecture as the following. Reference numeral 101R is a beam splitter, reference numeral 102R is a first relay lens, which is capable of moving on the optical axis, for changing a spherical refractive power loaded on the eye 5R. Reference numeral

15

103R and 104R are cylindrical lenses of which focal distance are equal, and both are capable of rotating about the optical axis to the same direction or the opposite direction. Still, in the case that the cylindrical component is produced, the rectification is performed by using the first relay lens 102R taking the spherical effect in consideration. Reference numeral 105R is a second relay lens. Reference numeral 106R is a target disk plate like a disk, and on which the same circumference, a fixation chart for making an examined eye fix at the time of the objective measurement, an all vision chart which plural targets having vision from 0.1 to 1.0 are drawn on one screen, a respective vision chart which targets every visions from 0.1 to 2.0 are respectively and separately drawn, and various kinds of inspection targets such as a dot point group chart and a red-green chart or the like for use in the subjective inspection. The target disc plate 106R is placed in a focus position of the second relay lens 105R, and it changes over and places the various kinds of targets on the light path by driving and rotating a motor which is not shown. Reference numeral 107R is a condenser lens and reference numeral 108R is an illumination lamp.

The target indicating optical system 100L has a right and left symmetrical optical system against the target indicating optical system 100R (marks L are attached to respective constructive parts instead of R, and thereby the description is omitted). Additionally, the target indicating optical system 100R and 100L are respectively constructed so as to be capable of moving right and left in response to the interpupilary distance between the right eye 5R and the left eye 5L.

(Objective refractive power measurement-Alignment-Observation optical system)

The rotation mirror 109 is disposed between a beam splitter 101R and 101L, and when the objective measurement is performed, the light path is changed over in response to the side of right and left of measurement eyes. Behind the rotation mirror 109, the objective refractive power measurement-Alignment-Observation optical system 110 same as the first preferred embodiment is disposed (the description of these optical system is omitted by invoking the mention of the first preferred embodiment).

Figure 13:
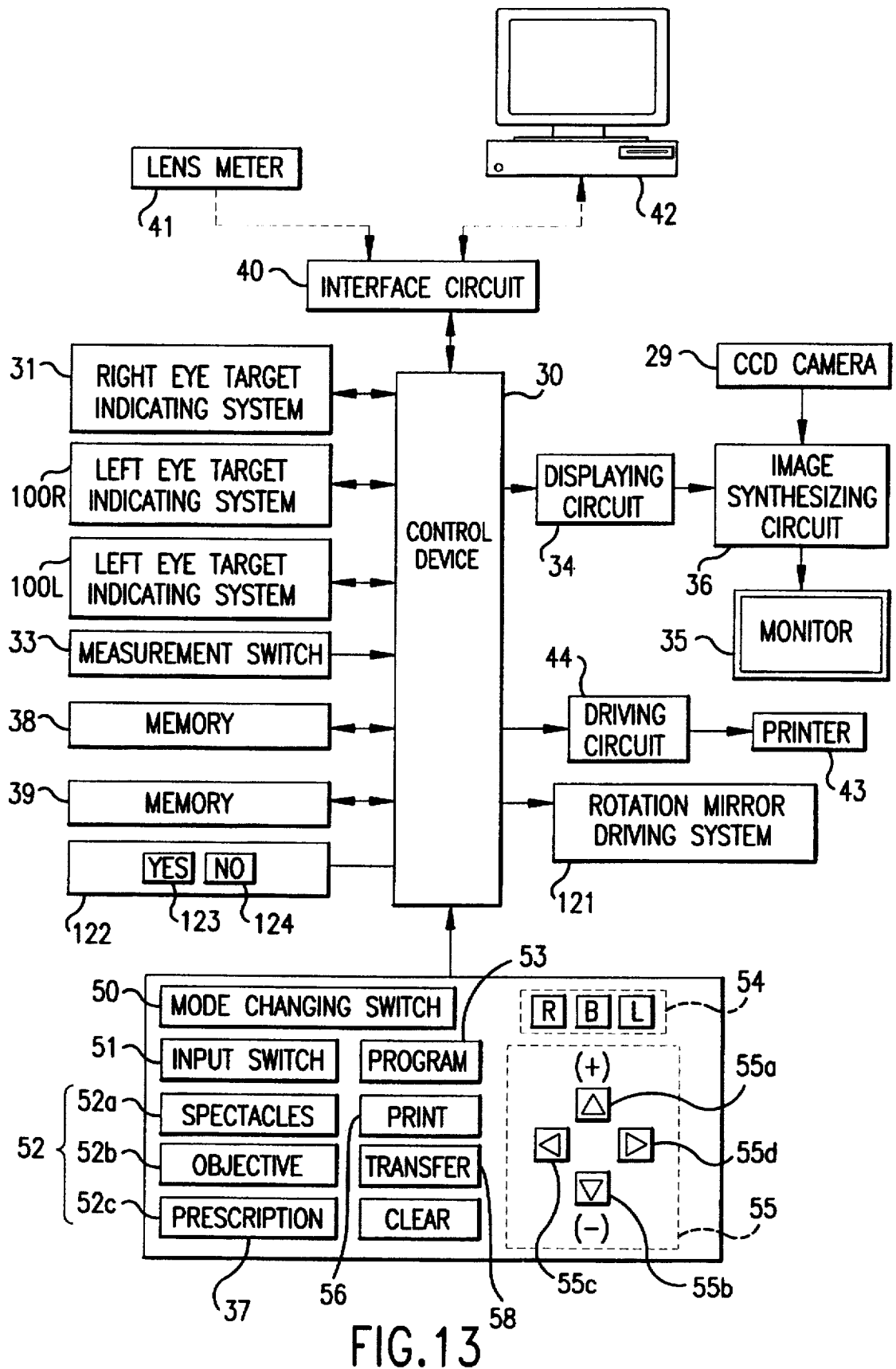
FIG. 13 is a view showing an important part of a control system of an apparatus according to the second preferred embodiment of the present invention.

FIG. 13 is a view showing an important part of a control system of an apparatus according to the second preferred embodiment of the present invention. The same marks are attached to the factors which has the same function as the first preferred embodiment, and thereby the description is omitted. Reference numeral 100R is a right eye target indicating system and reference numeral 100L is a left eye target indicating system, and the target indicated to the examined eye and the refractive power given to the eye can be changed by control of the control device 30. Reference numeral 121 is a rotation mirror driving system for driving the rotation mirror 109. Reference numeral 122 is a response switch for an examinee, which is provided YES-key 123 and NO-key 124.

The operation of the apparatus which has the above mentioned construction will be described below. Since the apparatus has a subjective inspection function, so the measurement mode can be changed over to an objective refractive power measurement mode, an unaided eye vision measurement mode, a previous spectacles vision measurement mode, a subjective refractive power measurement mode, or a vision confirmation mode or the like by using the mode changing switch 50. Still, in the case that the examinee has his own spectacles, the spectacles is measured by using the lens meter 41, and thereby the data of previous spectacles value is inputted in a manner same as the first preferred embodiment.

16

(A) Objective refractive power measurement

The mode is changed to the objective refractive power measurement mode by using the mode changing switch 50, and then the fixation targets of the target disc plates 100R and 100L are respectively set on the respective light paths of the target indicating optical systems 106R and 106L. The rotation mirror 109 is rotated by depressing the R switch or L switch in the selection switch 54 for determining the measurement eye. The examiner adjusts a space between the target indicating optical system 100R and the target indicating optical system 100L with the examiner's eyes respectively observing images of anterior portions of the eyes to be examined of right and left displayed on the monitor 35, and thereby the examiner performs the alignment by making the apparatus move before and behind against the examined eye. After the alignment for right eye and left eye has been completed, the examiner depresses the R switch or L switch in the selection switch 54 and thereby the measurement eye is selected, and then the objective refractive power measurement is executed by the apparatus (hereinafter the description is continued by regarding it as the right eye is selected). The control device 30 makes the objective refractive power measurement system 31 go into run, and thereby it obtains objective measuring values (The objective measurement is same as the first preferred embodiment).

The control device 30 obtains a value of an estimated unaided eye vision based on the objective measuring data. The means for obtaining the value of the estimated unaided eye vision classifies the value of the objective measuring value into 4 types as mentioned below and performs the operation based on the table E of visual acuity values based on the myopia power shown in FIG. 14(a) and the table F of accommodation powers in response to ages shown in FIG. 14(b). These tables are stored in memory 33 in advance (in the preferred embodiment, it is regarded that the value of CYL is read by way of minus-reading.

(1) In the case that the value of SPH of objective measurement is 0 or minus and the value of CYL is 0 (only in the case of regular vision or myopia)

The estimated unaided eye vision in response to the value of SPH (myopia power) is obtained from the table E.

(2) In the case that the value of SPH of objective measurement is 0 or minus and the value of CYL is not 0 (only in the case of astigmatism or in the case of myopia inclusive astigmatism)

The value of CYL is defined as equal to the value of SPH, and then the estimated unaided eye vision is obtained from the table E on the basis of the value obtained by adding the value of SPH to the value of CYL.

Still, as another way, it is considered that the value of estimated unaided eye vision is obtained from the table E on the basis of the value of equivalent spherical surface which is obtained by adding a half of the value of CYL to the value of SPH. These two method can be selected by an examinee based on his course in advance.

(3) In the case that the value of SPH of the objective measurement is plus and the value of CYL is 0 (only in the case of hyperopia)

In the case of hyperopia, the effect of an accommodation power is large, therefore the accommodation power suitable for the age is obtained from the table F (the age of the examinee should be inputted in advance by using the input switch 51 after the confirmation by the case history or the like).

When the value is minus after subtracting the value of SPH calculated by the objective measurement from the accommodation power obtained from the table F in response to the age. the value of estimated vision is obtained from the table E by regarding a value of shortage for accommodation power as an appropriate myopia power. When the value after subtracting the value of SPH from the accommodation power is 0 or plus. the estimated vision is defined as 1.0 by regarding the myopia power in the table E as 0.

(4) In the case that the value of SPH of the objective measurement is plus and the value of CYL is not 0 (in the case of hyperopia inclusive of astigmatism)

When the value is plus after subtracting the value of SPH calculated by the objective measurement from the accommodation power obtained from the table F on the basis of the age. the value of estimated vision is obtained from the table E on the basis of the value obtained by adding the value of CYL to the calculated-value. When the value obtained by subtracting the value of SPH from the accommodation power is 0 or plus. the value of estimated vision is obtained from the table E only on the basis of the value of CYL.

The value of estimated unaided eye vision obtained by the operation from (1) to (4). together with the data of objective measuring value. is stored in the memory 39. Additionally. the result of the measurement (and the value of estimated unaided eye vision) is displayed at the monitor 35.

(B) The measurement of unaided eye

Successively. the mode is changed to the unaided eye measurement mode (it is considered as another way that this mode is designated before the objective refractive power measurement so that the mode may be automatically changed to this mode after the objective refractive power measurement). If the changing signal of the measurement mode is outputted. the control device 30 makes the disc-plate-motor drive and makes the target disc plate 106R rotates, and thereby the respective vision chart is set which has the targets of the estimated unaided eye vision value obtained as described above. on the light path as an initial value. The examiner starts the unaided eye vision measurement of the examined eye under this target indicating condition. The examiner asked the examinee whether he can decipher the target or not. and the examiner changes over the respective vision chart according to the examinee's response by operating the upper-direction switch 55a and the lower-direction switch 55b for changing a vision. The value of unaided eye vision decided upon by an operation of switches (or a mode changing signal) is displayed on the monitor 35 and stored in the memory 39.

(C) The previous spectacles measurement

In the case that the examinee has his own spectacles (including the case of a contact lens). after the unaided eye vision measurement. a previous spectacles measurement based on the spectacles power measured in advance is performed.

If a changing signal for changing the mode to the previous spectacles measurement mode. thereafter the control device 30. based on the data of previous spectacles value. moves the first relay lens 102R and rotates the cylindrical lenses 103R and 104R and thereby the optical system is adjusted and disposed in response to the data of previous spectacles value.

Figure 15A:
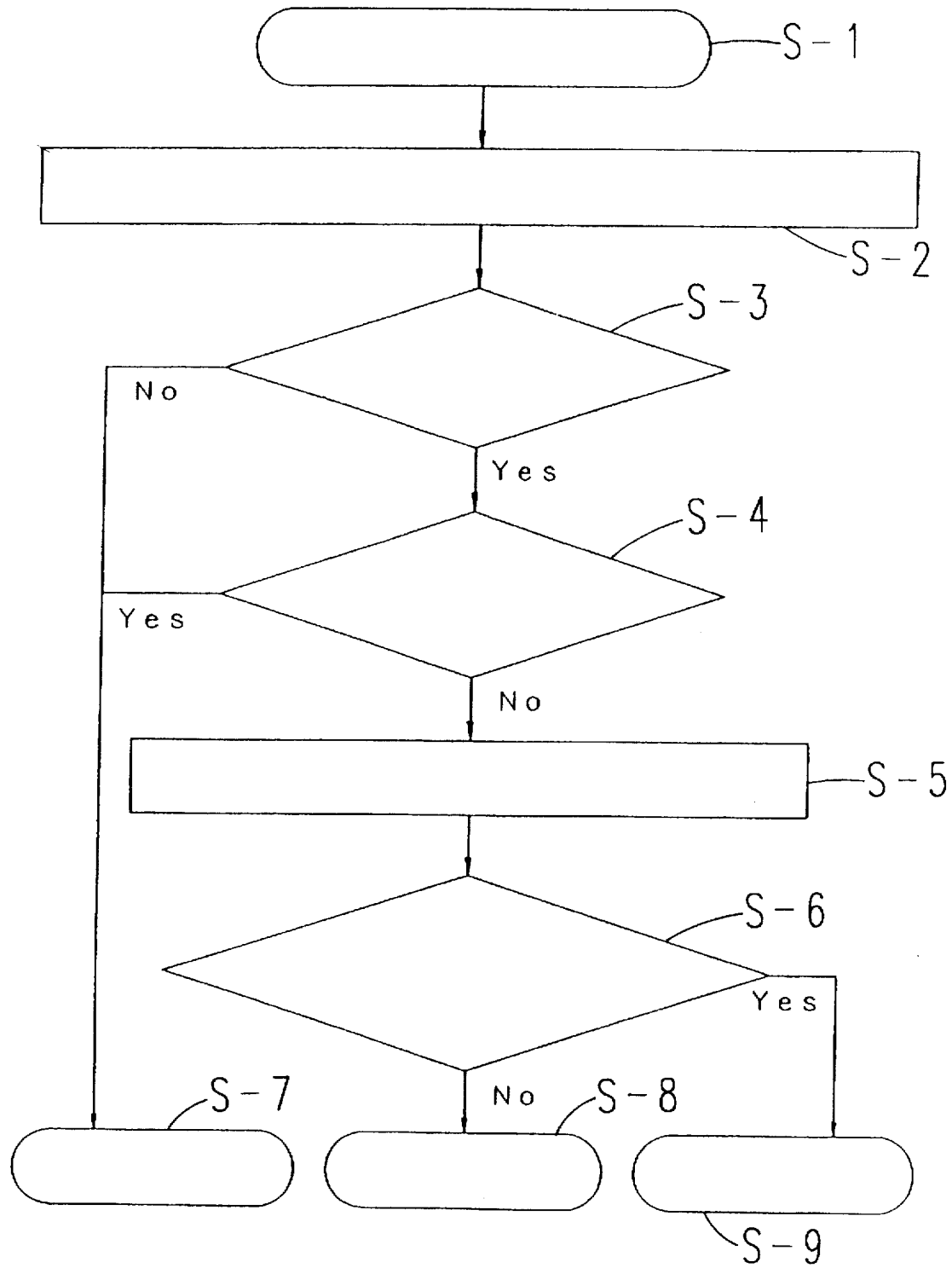

Additionally. the control device 30 places the respective vision chart on the light path by rotating the target disc plate 106R. at this time. the vision value of the chart is decided as described below (see a flowchart shown in FIG. 15).

At first. the residual power is calculated on the basis of the data of objective measurement and the data of previous spectacles measurement. and as well as an estimation of an unaided eye vision value (performing the process to move from the residual power to the objective measuring data). the estimated vision value by using the previous spectacles is obtained from the tables E and F shown in FIGS. 14(a) and 14(b) based on the calculated-residual power.

Next. the actual value of the unaided-eye vision which is obtained in the previous stage is compared with the estimated value of the unaided-eye vision. if these are equal to each other. the estimated vision value which is obtained on the basis of the residual power, which is left intact. is defined as the vision value which is initially desired (as well as in the case that there is not an actual data of an unaided eye vision value).

When the actual value of the unaided-eye vision is different from the estimated value of the unaided-eye vision. the possibility of which the estimated vision value by using the previous spectacles is different from the actual previous spectacles vision is high. therefore the rectification is added to the estimated vision value obtained from the residual power. For example. to make the description easier. if the examined eye of which the value of CYL is 0 exclusive astigmatism is considered. in the case that the SPH-value of the objective measurement value data is −2.00D (diopter) and the SPH-value of the data of previous spectacles value is −1.00D. the residual power is −1.00D. According to the table E shown in FIG. 14(a). an estimated vision value of an unaided eye is 0.2 and the estimated vision value of the previous spectacles is 0.6. At this time. in the case that the actual unaided eye vision value is 0.4. the myopia power corresponding to this one is −1.50D according to the table E. therefore the difference −0.50D between −1.50D of the myopia power and −2.00D of the objective measurement value data is the rectifying quantity. That is. the rectified-residual power is −0.50D by subtracting the rectifying quantity −0.50D from the rectifying power −1.00D. the estimated vision value of the previous spectacles corresponding to this one is 0.8 according to the table E (this is in the case that the actual vision value is more than the estimated unaided eye vision value. however in the case that the actual value is less than the estimated value. the rectification is added as the same way described above). As described above. the rectified value of the estimated vision by using the previous spectacles is obtained by adding the rectification to the value of the estimated vision obtained from the residual power. Still. upon obtaining this rectified value of the estimated vision. in the case that the rectified residual power is plus. the rectified value of the estimated vision is defined as 1.0. Additionally. in the case that the actual value of the unaided eye vision is less than or equal to 0.1. the rectified value of the estimated vision is defined as the smaller one among the absolute values of myopia powers corresponding to respective values of the unaided eye vision since there are plural myopia values corresponding to the value of the unaided eye vision according to the table E of the preferred embodiment.

After the rectified value of the estimated vision by using the previous spectacles is obtained. successively. this rectified value of the estimated vision is compared with the actual value of the unaided eye vision. in the case that the rectified value of the estimated vision is lower. the actual value of the unaided eye vision is defined as the initial desired vision value. in the case except it. the rectified value of the estimated vision by using the previous spectacles is defined as the initial desired vision value.

When the respective vision chart. obtained in a manner as described above. is disposed in the light path by an initial desire. as well as the unaided eye vision measurement mentioned above, the examiner changes over the respective vision chart which is indicated, according to the response from the examinee by operating the upper-direction switch 55a and the lower-direction switch 55b. The value of unaided eye vision by using the previous spectacles is displayed on the monitor 35 and stored in the memory 39.

(D) Subjective refractive power measurement

When the mode is changed to the subjective refractive power measurement mode, on the light path of the target indicating optical system 100R of the measurement eye side, based on the data of objective value, the first relay lens 102R, the cylindrical lenses 103R and 104R are drove, and thereby the optical system of the refractive power corresponding to the objective value is set up to the initial position. Additionally, the target having the vision value of 1.0 as the target for the target disc plate 106R is disposed in the light path.

The examiner makes the examinee respond the condition-to-see of the target by using the YES-key 123 and the NO-key 124 in the response switch 122. In the case that the examiner can decipher the indicating target, if the examiner depresses the YES-key, the target having 1 grade higher than the target of the initial indication. After that, according to the response that whether the examiner can decipher the target which is indicated or not, the NO-key 124 is depressed, since the data of object value is to be in low-correction, −0.25D is added to the correcting optical system of the initial desire, and then the target which could not been deciphered is indicated. By repeating this operation, it is decided that the S-value (spherical power) closest to a plus when the maximum vision value is obtained finally is the corrected-power by the subjective measurement. Thereby the accurate S-value of the examined eye is obtained. About the C-value and the A-value, in almost all the case, it is allowed to adopt the data of objective value, kept as it is, therefore the value is defined as the basis for the power adjustment. Also, the vision value is inputted based on the target which is indicated at the time when the S-value is obtained.

Still, in the measurement of the subjective refractive power, it can be allowed to obtain the S-value by indicating the red/green target. Additionally, as well as the general subjective measurement, it is allowed to detect the axis of astigmatism and the power of astigmatism. In this case, the inspection can be easily performed by storing the procedure of the inspection as a program.

(E) Confirmation for the vision value

After the objective refractive power measurement and the subjective refractive power measurement every on eye are finished, if the mode is changed to the vision confirmation mode, the corrective optical system having the refractive power based on the respective subjective measurements in the target indicating systems both of right and left, and as the indicating target, the vision inspecting target having the vision value higher than either right eye or left eye. According to this, the vision confirmation for both eyes is performed. On the basis of the response by the examinee for the condition-to-see, if the upper-direction switch 55a is depressed, the indicating target is changed-over to the target having 1 grade higher, and if the lower-direction switch 55b is depressed, the indicating target is changed to the target having 1 grade lower (it is can be allowed to change-over the targets based on the input of the YES-key 123 and the NO-key 124 by the examinee-own).

(F) Calculation for the standard power of the prescribed value

After the previous spectacles values are inputted and the subjective values by the subjective refractive power measurement for respective eyes are performed, and then if the program switch 53 is depressed, the apparatus calculates the standard power of the prescribed value which is expected most suitable for the examinee in response to the automatic adjustment program. The automatic adjustment program for use in the second preferred embodiment is the same as the one for use in the first preferred embodiment basically. However, after the subjective refractive power measurement, the calculation is based on the S-value (when the C-value is adjusted, the value is included) which is adjusted against the objective value. The standard power of the prescribed value, which is calculated by the apparatus, is displayed at the monitor 35.

Respective measurement results, as measured above, are printed out from the printer 43 by depressing the print switch 56.

The preferred embodiments described above, the description is about the eye-refractive power measuring apparatus provided the subjective inspecting function, however the preferred embodiment may be applied to the apparatus combined with the target indicating device and the eye-refractive power measuring apparatus. Additionally, in the case of the apparatus which does not have the function (subjective inspecting function), the examiner is informed of the estimated value information of the unaided eye vision which is obtained on the basis of the objective measuring data, by displaying these data at the monitor or printing out (or by transferring these data to another ophthalmic apparatus), and thereby the examiner, by utilizing this information, can achieve to increase efficiency in the vision inspection in the case that the examiner performs the temporary frame inspection or the like. As the preferred embodiment, the previous spectacles measurement data measured by a lens meter is made to be capable of inputting into the eye-refractive power measuring apparatus, and thereby the apparatus can obtain the estimated vision value for the previous spectacles on the basis of the difference against the objective measuring data, therefore if this is informed to the examiner, he can utilize this information for the inspection.

The present invention may be embodied in other specific forms without departing from the spirit or essential characteristics thereof. For instance, in the preferred embodiment, the rectifying quantities $\Delta$ S1, $\Delta$ S2, $\Delta$ S3, $\Delta$ S4 for the rectifying process from A1 to D1 are obtained by calculation, however these values, together with the tables, are prepared in advance, and thereby he may obtain required data according to them.

The forgoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications are suited to the particular use contemplated. It is intended that the scope of the invention be defined by the claims appended hereto, and their equivalents.

What is claimed is:

1. An ophthalmic apparatus for obtaining a refractive corrected power based on a refractive power that an eye to be examined has, the apparatus comprising:

input means for inputting data of objective values obtained by measuring objectively the refractive power of an eye to be examined and information of adjustment factors for adjusting a corrected power;

program storing means for storing a program in order to adjust the corrected power against the data of objective values based on the data inputted by said input means and for expecting a prescribed power;

executing means for executing the program stored in said program storing means;

prescribed power calculating means for calculating an expected-prescribed power in response to the program executed by said executing means; and displaying means for displaying the expected-prescribed power calculated by said prescribed power calculating means.

2. An ophthalmic apparatus according to claim 1, is an eye-refractive power measuring apparatus which comprises objective refractive power measuring means for measuring objectively a refractive power of the eye based on projecting a target for a measurement onto a fundus of the eye to be examined and detecting a light bundle of a target image transmitted from a fundus of the eye by means of photo-detecting elements.

3. An ophthalmic apparatus according to claim 2, further comprises, unaided-eye visual acuity estimating means for estimating a visual acuity value of an unaided-eye based on objective measuring data obtained by said objective refractive power measuring means; and output means for outputting an estimated-result by said unaided-eye visual acuity estimating means.

4. An ophthalmic apparatus according to claim 3, further comprises displaying means for displaying said estimated-result.

5. An ophthalmic apparatus according to claim 3, wherein said unaided-eye visual acuity estimating means estimates a visual acuity value of an unaided-eye based on a table of visual acuity values corresponding to spherical powers in order to apply under the condition that objective measuring data are myopia.

6. An ophthalmic apparatus according to claim 3, wherein said unaided-eye visual acuity estimating means estimates a visual acuity value of an unaided-eye based on a table corresponding to both an age of an examinee and a spherical power in order to apply under the condition that objective measuring data are hyperopia.

7. An ophthalmic apparatus according to claim 3, wherein said unaided-eye visual acuity estimating means further comprises means for astigmatism processing means for rectifying a visual acuity of an unaided-eye under the condition that astigmatism exists in objective data.

8. An ophthalmic apparatus according to claim 3, further comprises transfer means for transferring data to a device capable of indicating a target.

9. An ophthalmic apparatus according to claim 2, further comprises, input means for inputting measuring data of previous spectacles, which are obtained by lens meter for measuring a power of spectacles or contact lens; and previous spectacles visual acuity value estimating means for estimating a visual acuity value of previous spectacles based on a residual power which is calculated on the basis of the comparison between said visual acuity value of previous spectacles and the objective measuring data.

10. An ophthalmic apparatus according to claim 9, further comprises, unaided-eye visual acuity estimating means for estimating a visual acuity value of an unaided-eye based on objective measuring data obtained by said objective refractive power measuring means;

unaided-eye visual acuity measuring means for measuring a visual acuity of an eye to be examined by indicating an inspecting target for use in a visual acuity inspection; and visual acuity rectifying means for rectifying the estimated-visual acuity value of previous spectacles obtained by said previous spectacles visual acuity value estimating means on the basis of the comparison between the actual-measured visual acuity value of the unaided-eye that is obtained by said unaided-eye visual acuity measuring means and the estimated visual acuity value of the unaided-eye that is obtained by said unaided-eye visual acuity estimating means.

11. An ophthalmic apparatus according to claim 9, wherein said previous spectacles visual acuity value estimating means estimates a visual acuity value of an unaided-eye based on a visual acuity table corresponding to a spherical power in order to apply under the condition that the objective measuring data are myopia.

12. An ophthalmic apparatus according to claim 9, wherein said previous spectacles visual acuity value estimating means estimates a visual acuity value of an unaided-eye based on a table corresponding to both an age of an examinee and a spherical power in order to apply under the condition that objective measuring data are hyperopia.

13. An ophthalmic apparatus according to claim 9, wherein said previous spectacles visual acuity estimating means further comprises astigmatism processing means for rectifying a visual acuity of a previous spectacles under the condition that astigmatism exists in a residual power.

14. An ophthalmic apparatus according to claim 2, is an eye-refractive power measuring apparatus which further comprises subjective refractive power measuring means, which has target indicating optical system, which indicates a target for use in a subjective inspection and involves corrective optical system capable of adjusting a refractive power, for measuring a subjective refractive power of an eye to be examined on the basis of the adjustment by said corrective optical system.

15. An ophthalmic apparatus according to claim 1, wherein said information of adjustment factors inputted by said input means includes a distance information which an examinee uses spectacles, and said prescribed power calculating means includes means for rectifying a corrected power based on said distance information.

16. An ophthalmic apparatus according to claim 1, wherein said information of adjustment factors inputted by said input means includes an information which concerns to an adopting capacity against a variation of a corrected power of an eye to be examined, the program which is stored in said program storing means has at least 2 kinds of rectifying-quantity in response to the difference of the adopting capacity against the variation of the eye to be examined.

17. An ophthalmic apparatus according to claim 16, wherein the information which concerns to an adopting capacity is an information of an age of an examinee.

18. An ophthalmic apparatus according to claim 1, wherein said prescribed power calculating means includes means for obtaining a rectifying-quantity for use in an adjustment of a corrected power based on the inputted-data of the objective value by means of either a rectification table or a calculation.

19. An ophthalmic apparatus according to claim 18, wherein the rectifying-quantity obtained by said prescribed power calculating means is based on at least one of a spherical power and an astigmatism power of data of objective values.

20. An ophthalmic apparatus according to claim 18, wherein the information of adjustment factors inputted by said input means includes an information which concerns a refractive power of a refractive power corrective tool, the rectifying-quantity obtained by said prescribed power calculating means is based on a power difference between a data of objective value and at least either a spherical power or an astigmatism power of refractive power information of a refractive power corrective tool.

21. An ophthalmic apparatus for obtaining a refractive corrected power based on a refractive power that an eye to be examined has, the apparatus comprising:

objective refractive power measuring means for measuring objectively a refractive power of an eye to be examined based on projecting a target for a measurement onto a fundus of the eye to be examined and detecting a light bundle of a target image transmitted from the fundus of the eye by means of photo-detecting elements;

subjective refractive power measuring means that has target indicating optical system which indicates a target for use in a subjective inspection and involves corrective optical system capable of adjusting a refractive power, for measuring a subjective refractive power of the eye to be examined on the basis of the adjustment by said corrective optical system;

input means for inputting information of adjustment factors for adjusting a corrected power;

program storing means for storing a program in order to adjust the corrected power against the data of the subjective value based on the data inputted by said input means and for expecting a prescribed power;

executing means for executing the program stored in said program storing means;

prescribed power calculating means for calculating an expected-prescribed power in response to the program executed by said executing means; and displaying means for displaying the expected-prescribed power calculated by said prescribed power calculating means.

22. An ophthalmic apparatus according to claim 21, wherein said information of adjustment factors inputted by said input means includes a distance information which an examinee uses spectacles, and said prescribed power calculating means includes means for rectifying a corrected power based on said distance information.

23. An ophthalmic apparatus according to claim 21, wherein said information of adjustment factors inputted by said input means includes an information which concerns to an adopting capacity against a variation of a corrected power of an eye to be examined, the program which is stored in said program storing means has at least 2 kinds of rectifying-quantity in response to the difference of the adopting capacity against the variation of the eye to be examined.

24. An ophthalmic apparatus according to claim 23, wherein the information which concerns to an adopting capacity is an information of an age of an examinee.

25. An ophthalmic apparatus according to claim 21, wherein said prescribed power calculating means includes means for obtaining a rectifying-quantity for use in an adjustment of a corrected power based on the inputted-data of the objective value by means of either a rectify-table or a calculation.

26. An ophthalmic apparatus according to claim 25, wherein the rectifying-quantity obtained by said prescribed power calculating means is based on at least one of a spherical power and an astigmatism power of data of objective values.

27. An ophthalmic apparatus according to claim 25, wherein the information of adjustment factors inputted by said input means includes an information which concerns a refractive power of a refractive power corrective tool, the rectifying-quantity obtained by said prescribed power calculating means is based on a power difference between a data of objective value and at least either a spherical power or an astigmatism power of refractive power information of a refractive power corrective tool.

28. An ophthalmic apparatus according to claim 21, further comprises response input means for inputting a response which concerns to condition-to-see by an examinee in person, wherein said subjective refractive power measuring means includes control means for driving said target indicating optical system based on an input signal inputted by using said response input means.

* * * * *